(12) United States Patent
Mercep et al.

(10) Patent No.: US 7,109,176 B2
(45) Date of Patent: *Sep. 19, 2006

(54) NONSTEROIDAL ANTI-INFLAMMATORY SUBSTANCES, COMPOSITIONS AND METHODS FOR THEIR USE

(75) Inventors: Mladen Mercep, Zagreb (HR); Milan Mesic, Zagreb (HR); Linda Tomaskovic, Zagreb (HR); Stribor Markovic, Zagreb (HR)

(73) Assignee: Pliva-Istrazivacki Institut D.o.o., Zagreb (HR)

( * ) Notice: Subject to any disclaimer, the term of this patent is extended or adjusted under 35 U.S.C. 154(b) by 0 days.

This patent is subject to a terminal disclaimer.

(21) Appl. No.: 10/615,010

(22) Filed: Jul. 7, 2003

(65) Prior Publication Data

US 2004/0097434 A1 May 20, 2004

Related U.S. Application Data

(60) Provisional application No. 60/394,671, filed on Jul. 8, 2002.

(51) Int. Cl.
*A61K 31/70* (2006.01)
*C07H 17/08* (2006.01)

(52) U.S. Cl. .............................. 514/29; 514/8; 530/322; 536/7.2; 536/7.4

(58) Field of Classification Search .................. 514/8, 514/29; 530/322; 536/7.2, 7.4
See application file for complete search history.

(56) References Cited

U.S. PATENT DOCUMENTS

| | | | |
|---|---|---|---|
| 4,474,768 A | 10/1984 | Bright | |
| 5,004,731 A | 4/1991 | Philippe et al. | |
| 6,127,355 A | 10/2000 | Greenwald et al. | |
| 6,566,509 B1 * | 5/2003 | Griffin et al. | 536/7.4 |
| 2001/0006962 A1 | 7/2001 | Myhren et al. | |
| 2004/0005641 A1 | 1/2004 | Burnet et al. | |
| 2004/0033969 A1 | 2/2004 | Burnet et al. | |
| 2004/0087517 A1 * | 5/2004 | Burnet et al. | |
| 2004/0186063 A1 * | 9/2004 | Gutke et al. | |

FOREIGN PATENT DOCUMENTS

| | | |
|---|---|---|
| EP | 0 283 055 | 9/1998 |
| EP | 0 895 999 | 2/1999 |
| EP | 0984019 | 3/2000 |
| EP | 1 046 394 | 10/2000 |
| GB | 2 327 084 | 1/1999 |
| WO | WO-97/41255 | 11/1997 |
| WO | WO 98/56801 | 12/1998 |
| WO | WO-99/28308 | 6/1999 |
| WO | WO-99/64040 | 12/1999 |
| WO | WO 00/64882 | 11/2000 |
| WO | WO-02/15700 | 2/2002 |
| WO | WO-02/055531 | 7/2002 |
| WO | WO-03/070173 A2 | 8/2003 |
| WO | WO-03/070174 A2 | 8/2003 |
| WO | WO-03/070254 | 8/2003 |

OTHER PUBLICATIONS

Burnett et al., "Conjugates of biologically active compounds, methods for their preparation and use, formation, and pharmaceutical applications thereof," U.S. Appl. No. 60/357,789, filed Feb. 15, 2002.

Brandt–Rauf et al., "Fluorescent Assay For Estimating the Binding of Erythromycin Derivatives to Ribosomes," Antimicrobial Agents and Chemotherapy, American Society for Microbiology, Washington, D.C., 14(1):88–94. (1978).

Gladue R. P. et al., "In Vitro and In Vivo Uptake of Azithromycin (CP–62,993) by Phagocytic Cells: Possible Mechanism of Delivery and Release at Sites of Infection," *Antimicrob. Agents and Chemother.*, 33. 1989, 277–282.

Olsen K. M. et al., "Intrapulmonary Pharmacokinetics of Zithromycin in Healthy Volunteers Given Five Oral Doses," *Antimicrob. Agents and Chemother.*,40, 1996, 2582–2585.

Mikasa, K. et al., "The anti–inflammatory effect of erythromycin in zymosan–induced peritonitis of mice,"*J. Antimicrob. Chemother.*, 30, 1992, 339–348.

"Discussion, Genomic organization of axolotl 1g genes," *J. Immunol.*, 159, 1997, 3395–4005.

Takizawa, H. et al., "Erythromycin Modulates IL–8 Expression in Normal and Inflamed Human Bronchial Epithelial Cells," *Am. J. Respir. Crit. Care Med.*, 156, 1997, 266–271.

Labro, M.T., "Anti–Inflammatory activity of macrolides: a new therapeutic potential?" *J. Antimicrob. Chemother.* 41, 1998, 37–46.

Denis A. et al., "Synthesis and Antibacterial Activity of HMR 36K47, A New Ketolide Highly Potent Against Erythromycin–Resistant and Susceptible Pathogens," *Bioorg. & Med. Chem. Lett*, 9, 1999, 3075–3080.

(Continued)

*Primary Examiner*—Elli Peselev
(74) *Attorney, Agent, or Firm*—Darby & Darby

(57) ABSTRACT

The present invention relates (a) to new compounds represented by Formula I:

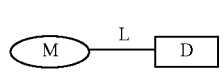

I wherein M represents a macrolide subunit (macrolide moiety) derived from macrolide possessing the property of accumulation in inflammatory cells, D represents a nonsteroidal subunit (nonsteroidal moiety) derived from non-steroid drug with anti-inflammatory, analgesic and/or anti-pyretic activity (NSAID) and L represents a linking group covalently linking M and D; (b) to their pharmacologically acceptable salts, prodrugs and solvates, (c) to processes and intermediates for their preparation, and (d) to their use in the treatment of inflammatory diseases and conditions in humans and animals.

45 Claims, No Drawings

OTHER PUBLICATIONS

Agouridas C. et al., "Synthesis and Antibacterial Activity of Ketolides (6–O–Methyl–3–oxoerythromycin Derivatives): A New Class of Antibacterials Highly Potent against Macrolide–Resistant and –Susceptible Respiratory Pathogens," *J. Med. Chem.*, 41, 1998, 4080–4100.

Sun, Or Y. et al. *J. Med. Chem.* 2000, 43, 1045–1049.

Denis A. et al., Synthesis of 6–O–Methyl–Azithromycin and Its Ketolide Analogue via Beckmann Rearrangement of 9(E)–6–O–Methyl–Erythromycin Oxime, *Bioorg. & Med. Chem. Lett.*, 8, 1998, 2427–2432.

Lartey et al., Synthesis of 4"–Deoxy Motilides: Identification of a Potent and Orally Active Prokinetic Drug Candidate, *J. Med. Chem.*, 38, 1998, 1793–1798.

Kirst, H.A. et al., "34. Metabolism of macrolides," Bryskier, A. J. et al., Ed. *Macrolides, Chemistry, Pharmacology and Clinical Use;* Bryskier, Amette Blackwell: Paris, 1993; pp. 485–491.

Ma, Z. et al., "Discovery and Development of Ketolides as a New Generation of Macrolide Antimicrobial Agents," *Current Medicinal Chemistry—Anti–Infective Agents*, 1, 2002, 15–34.

Pascual A. et al., "Uptake and Intracellular activity of ketolide HMR 3647 in human phagocytic and non–phagocytic cells," *Clin. Microbiol. Infect.*, 7, 2001, 65–69.

Hand, W. L. et al., "Characteristics and mechanisms of azithromycin accumulation and efflux in human polymorphonuclear leukocytes," *Int. J. Antimicrob. Agents*, 18, 2001, 419–425.

Amsden, G. W., "Advanced–generation macrolides: tissue–directed antibiotics," *Int. J. Antimicrob. Agents*, 18, 2001, 11–15.

Johnson, J. D. et al., "Antibiotic uptake by alveolar macrophages," *J. Lab. Clin. Med.*, 95, 1980, 429–439.

Wildfeuer, A. et al., "Uptake of Azithromycin by Various Cells and Its Intracellular Activity under In Vivo Conditions," *Antimicrob. Agents Chemother.*, 40, 1996, 75–79.

Scormeaux, B. et al., "Intracellular Accumulation, Subcellular Distribution, and Efflux of Tilmicosin in Chicken Phagocytes," *Poult. Sci.*, 77, 1998, 1510–1521.

Mtairag, E. M. et al., "Investigation of dirithromycin and erythromyclamine uptake by human neutrophils *in vitro*," *J. Antimicrob. Chemother.* 33, 1994, 523–536.

Anderson R. et al., "An in–vitro evaluation of the cellular uptake and intraphagocytic bioactivity of clarithromycin (A56268, TE–031), a new macrolide antimicrobial agent," *J. Antimicrob. Chemother.*, 22, 1988, 923–933.

Tasaka, Y. et al., "Rokitamycin Uptake by Alveolar Macrophages," *Jpn. J. Antibiot.* 41, 1988, 836–840.

Harf, R. et al., "Spiramycin uptake by alveolar macrophages," *J. Antimicrob. Chemother.*, 22, 1988, 135–140.

Suzuki, T. et al., "General and facile method for determination of configuration of steroid–17–yl–methyl glycolates at C–20 based on kinetic examination," *Chem. Soc., Perkin Trans.* 1, 1998, 3831–3836.

McLean, H.M. et al., "Novel Fluorinated Antiinflammatory Steroid with Reduced Side Effects: Methyl 9 α–Fluoroprednisolone–16–carboxylate," *J. Pharm. Sci.* 1994, 83, 476–480.

Little, R.J. et al., "Soft Drugs Based on Hydrocortisone: The Inactive Metabolite Approach and Its Application to Steroidal Antiinflammatory Agents," *Pharm. Res.*, 16, 1999, 961–967.

Kertesz, D.J. et al., "Thiol Esters from Steroid 17β–Carboxylic Acids: Carboxylate Activation and Internal Participation by 17α–Acylates," *J. Org. Chem.*, 51, 1986, 2315–2328.

Phillips, G. et al., "Synthesis and Structure—Activity Relationships in a Series of Antiinflammatory Corticosteroid Analogues, Halomethyl Androstane–17 β–carbothioates and 17β–carboselenoates," *J. Med. Chem.* 37, 1994, 3717–3729.

Bright, G.M. et al., "Synthesis, In Vitro and In Vivo Activity of Novel 9–Deoxo–9a–AZA–9a–Homoerythromycin A Derivatives; A new Class of Macrolide Antibiotics, The Azalides" *J. Antibiot.*, 41, 1998, 1029–1047.

Costa, A.M. et al., "Hybrids of macrolides and nucleobases or nucleosides," *Tetrahedron Letters*, 41, 2000, 3371–3375.

Luong et al., "Treatment options for Rheumatoid Arthritis: Celecoxib, Leflunomide, Etanercept, and Infliximab," *Ann. Pharmacother.* 34, 2000, 743–760.

Taketo, M.M., "Cyclooxygenase 2 Inhibitors in Tumorigenesis (Part II)," *J. Natl. Cancer Inst.* 90, 1998, 1609–1620.

Fournier, J., "COX–2 and Colon Cancer: Potential Targets for Chemoprevention," *J. Cell Biochem. Suppl.* 34, 2000, 97–102.

Carswell, E.A., et al., "An endotoxin–induced serum factor that causes necrosis of tumors," *Proc. Natl. Acad. Sci. USA* 72, 1975, 3666–3670.

Elliot, M., et al., "Randomised double–blind comparison of chimeric monoclonal antibody to tumour necrosis factor β (cA2) versus placebo in rheumatoid arthritis," *Lancet* 344, 1994, 1105–1110.

Mori, L., et al., "Attenuation of Collagen–Induced Arthritis in 55–kDa TNF Receptor Type 1 (TNFR1)IgG1–Treated and TNFR1–Deficient Mice," *J. Immunol.* 157, 1996, 3178–3182.

Pfeffer, K., et al., "Mice Deficient for the 55 kd Tumor Necrosis Factor Receptor Are Resistant Endotoxic Shock, yet Succumb to L. monocytogenes Infection," *Cell* 73, 1993, 457–467.

Georgopoulos, J., "Transmembrane TNF Is Sufficient To Induce Localized Tissue Toxicity and Chronic Inflammatory Arthritis in Transgenic Mice," *Inflamm.* 46, 1996, 86–97.

Keffer, J. et al., "Transgenic mice expressing human tumour necrosis factor: a predictive genetic model of arthritis," *Embo J.* 10, 1991, 4205–4031.

Van Assche, et al., "Anti–TNF agents in Crohn's disease," *Exp. Opin. Invest. Drugs* 9, 2000, 103–111.

Romo, D., et al., "Total Synthesis and Immunosuppresive Activity of (–)–Pateamine A and Related Compounds: Implementation of a α–Lactam–Based Macrocyclization," *J. Am. Chem. Soc.* 120, 1998, 12237–12254.

* cited by examiner

SEQUENCE LISTING

<160> NUMBER OF SEQ ID NOS: 4

<210> SEQ ID NO 1
<211> LENGTH: 31
<212> TYPE: DNA
<213> ORGANISM: Artificial Sequence
<220> FEATURE:
<223> OTHER INFORMATION: PCR primer

<400> SEQUENCE: 1
atataagctt gcgccatgag ccggagtctt c               31

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
atatggatcc tcagagctct gtggatggtc gc              32

<210> SEQ ID NO 3
<211> LENGTH: 28
<212> TYPE: DNA
<213> ORGANISM: Artificial Sequence
<220> FEATURE:
<223> OTHER INFORMATION: PCR primer

<400> SEQUENCE: 3
atataagctt gctgcgatgc tcgcccgc                   28

<210> SEQ ID NO 4
<211> LENGTH: 36
<212> TYPE: DNA
<213> ORGANISM: Artificial Sequence
<220> FEATURE:
<223> OTHER INFORMATION: PCR primer

<400> SEQUENCE: 4
atatggatcc ctacagttca gttcagtcga acgttc          36

NONSTEROIDAL ANTI-INFLAMMATORY SUBSTANCES, COMPOSITIONS AND METHODS FOR THEIR USE

This application claims priority to U.S. Provisional Application No. 60/394,671 filed Jul. 8, 2002, herein incorporated by reference in its entirety.

BACKGROUND OF THE INVENTION

The present invention relates to new anti-inflammatory compounds represented by the general structure I, to their pharmaceutically acceptable salts and solvates, to processes and intermediates for their preparation and to the use of these compounds in the treatment of inflammatory diseases and conditions in humans and animals.

SUMMARY OF THE INVENTION

Nonsteroid anti-inflammatory medicaments having different mechanisms of action act on particular inflammation mediators, thus providing a therapeutic effect. Due to differences not only in mechanisms of action but also in the particular inflammation mediators inhibited, the steroid and nonsteroid medicaments possess different profiles of anti-inflammation effects, hence certain medicaments may be more suitable than others for particular conditions. Moreover, most nonsteroid anti-inflammatory medicaments are not absolutely specific and their use is accompanied by unfavourable side-effects when used in greater dosages or over long periods of time. It is known that many nonsteroid anti-inflammatory medicaments act as inhibitors of endogenous COX-1 enzyme, which is very important in maintaining the integrity of the gastric mucosa. Thus, the use of these medicaments often causes injuries of the gastric mucosa and even bleeding. (Warner T. D. *Proc. Natl. Acad. Sci.* U.S.A. 1999, 96, 7563–7568.) Therefore, agents that selectively inhibit COX-2 but not COX-1 are preferable for treatment of inflammatory diseases Additionally, some anti-inflammatory compounds (such as theophylline) are known to have a very narrow therapeutic index, which limits their usage.

Recently, the nonsteroidal antiinflammatory drug celecoxib that specifically blocks COX-2 has been approved by the FDA for use in the treatment of rheumatoid arthritis (Luong et al. *Ann. Pharmacother.* 2000, 34, 743–760). COX-2 is also expressed in many cancers and precancerous lesions, and there is mounting evidence that selective COX-2 inhibitors may be useful for treating and preventing colorectal and other cancers (Taketo, M. M., *J. Natl. Cancer Inst.* 1998, 90, 1609–1620, Fournier et. al. *J. Cell Biochem. Suppl.* 2000, 34, 97–102).

Macrolides such as macrolide antibiotics accumulate preferentially within different cells of subjects administered such molecules, especially within phagocyte cells such as mononuclear peripheral blood cells, peritoneal and alveolar macrophages as well as in the liquid surrounding the bronchoalveolar epithelium (Glaude R. P. et al. *Antimicrob. Agents Chemother.,* 1989, 33, 277–282; Olsen K. M. et al. *Antimicrob. Agents Chemother.* 1996, 40, 2582–2585). Moreover, relatively weak inflammatory effects of some macrolides have been described. For example, the anti-inflammatory effect of erythromycin derivatives (Labro M. T. *J. Antimicrob. Chemother.,* 1998, 41, 37–46; WO 00/42055) and azithromycin derivatives has recently been described (EP 0283055). Anti-inflammatory effects of some macrolides are also known from in vitro and in vivo studies in experimental animal models such as zimosane-induced peritonitis in mice (Mikasa et al. *J. Antimicrob. Chemother.* 1992, 30, 339–348) and endotoxin-induced neutrophil accumulation in rat trachea (*J. Immunol.* 1997, 159, 3395–4005). The modulating effect of macrolides upon cytokines such as interleukin 8 (IL-8) (*Am. J. Respir. Crit. Care Med.* 1997, 156, 266–271) or interleukin 5 (IL-5) (EP 0775489 and EP 0771564) is known as well.

In 1975, TNF-α was defined as an endotoxin-induced serum factor causing tumor necrosis in vitro and in vivo (Carswell E. A. et al. *Proc. Natl. Acad. Sci. U.S.A.* 1975, 72, 3666–3670). In addition to antitumor activity, TNF-α has several other biologic activities, which are important in homeostasis as well as in pathophysiological conditions. The main sources of TNF-α are monocytes-macrophages, T-lymphocytes and mast cells.

The finding that anti-TNF-α antibodies (cA2) are effective in the treatment of patients suffering from rheumatoid arthritis (RA) (Elliot M. et al. *Lancet* 1994, 344, 1105–1110) intensified the interest to find new TNF-α inhibitors as possible potent medicaments for RA. Rheumatoid arthritis is an autoimmune chronic inflammatory disease characterized by irreversible pathological changes of the joints. In addition to RA, TNF-α antagonists are also applicable to several other pathological conditions and diseases such as spondylitis, osteoarthritis, gout and other arthritic conditions, sepsis, septic shock, toxic shock syndrome, atopic dermatitis, contact dermatitis, psoriasis, glomerulonephritis, lupus erhythematosus, scleroderma, asthma, cachexia, chronic obstructive lung disease, congestive heart failure, insulin resistance, lung fibrosis, multiple sclerosis, Crohn's disease, ulcerative colitis, viral infections and AIDS.

Proof of biological importance of TNF-α was obtained in in vivo experiments in mice having inactivated genes for TNF-α or its receptor. Such animals were resistant to collagen-induced arthritis (Mori L. et al. *J. Immunol.* 1996, 157, 3178–3182) and to endotoxin-induced shock (Pfeffer K. et al. *Cell* 1993, 73, 457–467). In experiments with animals having an increased TNF-α level, a chronic inflammatory polyarthritis appeared (Georgopoulos S. et al. *J. Inflamm.* 1996, 46, 86–97; Keffer J. et al. *EMBO J.* 1991, 10, 4025–4031), which was palliated by inhibitors of TNF-α production. The treatment of such inflammatory and pathologic conditions usually includes the application of non-steroid anti-inflammatory medicaments, in severe cases, however, gold salts, D-penicillinamine or methotrexate are administered. The mentioned medicaments act symptomatically and do not stop the pathological process. New approaches in therapy of rheumatoid arthritis have been established using medicaments such as tenidap, leflunomide, cyclosporin, FK-506 and biomolecules neutralizing the activity of TNF-α. At present, of the soluble TNF receptor named Etanercept (Enbrel, Immunex/Wyeth) and mouse and human chimeric monoclonal antibody named Infliximab (Remicade, Centocor) are available on the market. In addition to RA-therapy, etanercept and infliximab are also approved for the treatment of Crohn's disease (*Exp. Opin. Invest. Drugs* 2000, 9, 103).

New compounds represented by the Formula I, representing the subject of the present invention, their pharmacologically acceptable salts, hydrates, prodrugs and pharmaceutical compositions comprising them have hitherto not been described. Moreover, no compound representing the subject of the present invention has been described either as an anti-inflammatory substance or as an inhibitor of TNF-α or inhibitor of COX-1/COX-2 or an inhibitor of IL-1β. Consequently, the use of such <<hybrid>> macrolide/NSAID compounds to combat inflammatory states has not been described or suggested. Nor has there been a description or suggestion of pharmaceutical dosage forms containing effective amounts of a hybrid macrolide/NSAID compound for treating inflammatory states in a mammalian subject, including a human.

DETAILED DESCRIPTION OF THE INVENTION

Compounds of the Formula I differ from hitherto known ones in that they combine the antiinflammatory properties of the NSAID moiety with the accumulation properties afforded by the macrolide moiety, which, when conjoined, are recruited (along with the immune system cells in which macrolides preferentially accumulate) to the organs or tissues afflicted in inflammatory states, and result in substantially more localized and/or intensified abatement of the inflammation. Such action of the new compounds represented by the structure I arises from the macrolide portion M due to the specific pharmacokinetic properties of macrolides to acccumulate within immune cells of inflammatory profile, such as phagocytes, including polymorphonuclear cells, eosinophils, alveolar phagocytes, etc. Compounds of the Formula I posess improved pharmacokinetic and/or safety profiles, (even for those NSAIDs that are more selective COX-2 inhibitors) and present fewer and/or more benign side-effects.

Classical nonsteroidal anti-inflammatory drugs (NSAIDs) inhibit both COX-1 and COX-2 to varying extents. Indomethacin is also a nonselective COX inhibitor, but when linked to the macrolide moiety, it becomes a more selective COX-2 inhibitor which should significantly decrease and may even eliminate the gastrointestinal side effects of the parent compound. Even NSAIDs that are more selective inhibitors of COX-2, however, benefit from conjugation with the macrolides according to the present invention, at least because they become "targeted" to the locus of inflammation where they can exert an antiinflammatory effect while simultaneously their interaction with other tissues or physiological processes that would lead to side-effects. The compounds represented by the Formula I, which are the subject of the present invention, isomeric forms of such compounds, their pharmacologically acceptable salts, prodrugs, solvates and pharmaceutical compositions comprising them are not believed to have been previously described. Moreover, none of the compounds of the present invention has been described either as an anti-inflammatory substance or as an inhibitor of eosinophilic accumulation in organs or tissues.

The present invention is directed to (a) new "hybrid" compounds represented by the formula I

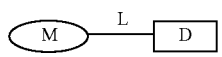

I wherein M represents a macrolide subunit possessing the property of accumulation in inflammatory cells, D represents a nonsteroidal anti-inflammatory subunit (NSAID) with anti-inflammatory, analgesic and/or antipyretic activity, and L represents a linking group covalently linking M and D;

(b) compositions containing one or more of the foregoing compounds in an amount effective to combat inflammation and thereby treat disorders and conditions involving inflammation in mammals, including humans; and (c) methods for using these compounds to treat such disorders and conditions.

The present compounds advantageously provide an improved therapeutic effect and/or an improved side effect profile.

Suitable macrolide subunits for the hybrid compounds of the present invention can be selected without limitation from multi-member lactonic ring molecules, wherein "member" refers to the carbon atoms or heteroatoms in the ring, and "multi" is a number greater than about 10, preferably from 10 to about 50, more preferably 12-, 14-, 15-, 16-, 17- and 18-member lactonic ring macrolides. 14- and 15-member ring macrolide subunits are particularly preferred, with azithromycin and its derivatives and erythromycin and its derivatives being most preferred.

More specific nonlimiting examples of molecules from which the macrolide subunit can be selected are the following:

(i) Macrolide antibiotics, including azalides, for example erythromycin, dirithromycin, azithromycin, 9-dihydro-9-deoxo-9a-aza-9a-homoerythromycin, HMR 3004, HMR 3647, HMR 3787, josamycin, erythromycylamine, ABT 773 flurithromycin, clarithromycin, tylosin, tilmicosin, oleandomycin, desmycosin, CP-163505, roxithromycin, miocamycin and rokitamycin and derivatives thereof, such as ketolides (e.g., 3-ketone), lactams (e.g., 8a- or 9a-lactams) and derivatives lacking one or more sugar moieties.

(ii) Macrolide immunosuppressants, such as FK 506, cyclosporin, amphotericin and rapamycin;

(iii) Macrolide antifungals with host cell inhibitory properties, such as bafilomycins, concanamycin nystatin, natamycin, candicidin, filipin, etruscomycin, trichomycin.

Methodologies for the synthesis of the above macrolides not commercially available and synthetic manipulation of macrolides in general are known to those of ordinary skill in the art, or may be found in: Denis A. et al. Bioorg. & Med. Chem. Lett 1999, 9, 3075–3080; Agouridas C. et al. J. Med. Chem. 1998, 41, 4080–4100; and EP-00680967 (1998); Sun Or Y. et al. J. Med. Chem. 2000, 43, 1045–1049; U.S. Pat. No. 05,747,467 (1998); McFarland J. W. et al. J. Med. Chem. 1997, 40, 1041–1045; Denis A. at al. Bioorg.& Med. Chem. Lett. 1998, 8, 2427–2432; WO-09951616*(1999); Lartey et al. J. Med Chem. 1995, 38, 1793–1798; EP 0984019; WO 98/56801, herein incorporated by reference in their entirety.

Additional suitable macrolides are known, some being disclosed in Bryskier, A. J. et al. *Macrolides, Chemistry, Pharmacology and Clinical Use*; Arnette Blackwell: Paris, 1993, pp 485–491, 14(R)-hydroxyclarithromycin, erythromycin-11,12-carbonate, tri-O-acetyloleandomycin, spiramycin, leucomycin, midecamycin, rasaramycin incorporated by reference in its entirety; in Ma, Z. et al. *Current Medicinal Chemisty-Anti-Infective Agents*, 2002, 1, 15–34; also incorporated by reference in its entirety pikromycin, narbomycin, HMR-3562, CP-654743, CP-605006, TE-802, TE-935, TE-943, TE-806, 6,11-bridged ketolides, CP-544372, FMA-199, A-179461; and in Romo, D. et al. *J. Am. Chem. Soc.* 1998, 120; 12237–12254; also incorporated by reference in its entirety. See, in particular the structures and derivatives for 14- and 16-member ring macrolides at pp 487–491 of Bryskier, et al., and the various ketolide derivatives and syntheses in Ma et al., notably in all the structure tables and all the reaction schemes. All these macrolides after being conjugated to NSAIDs are within the scope of the present invention. The foregoing specifically named or referenced macrolide compounds are commercially available or methods for their syntheses are known.

It is important that the macrolide subunit derive from a macrolide having the property of accumulating within immune system cells recruited to the site of inflammation, especially phagocytic cells. Most of the lactonic compounds defined above are known to have this property. For example, 14-membered macrolides such as erythromycin and its derivatives; 15-membered macrolides such as azithromycin and its derivatives, as well as 8a- and 9a-lactams and their derivatives; 16-membered macrolides such as tilmicosin, desmycosin; and spiramycin.

Additional examples of macrolides accumulating within specific classes of cells may be found in: Pascual A. et al. Clin. Microbiol. Infect. 2001, 7, 65–69. (Uptake and intracellular activity of ketolide HMR 3647 in human phagocytic and non-phagocytic cells); Hand W. L. et al. Int. J. Antimicrob. Agents, 2001, 18, 419–425. (Characteristics and mechanisms of azithromycin accumulation and efflux in human polymorphonuclear leukocytes); Amsden G. W. Int. J. Antimicrob. Agents, 2001, 18, 11–15. (Advanced-generation macrolides: tissue-directed antibiotics); Johnson J. D. et al. J. Lab. Clin. Med. 1980, 95, 429–439. (Antibiotic uptake by alveolar macrophages); Wildfeuer A. et al. Antimicrob. Agents Chemother. 1996, 40, 75–79. (Uptake of azithromycin by various cells and its intracellular activity under in vivo conditions); Scorneaux B. et al. Poult. Sci. 1998, 77, 1510–1521. (Intracellular accumulation, subcellular distribution, and efflux of tilmicosin in chicken phagocytes); Mtairag E. M. et al. J. Antimicrob. Chemother. 1994, 33, 523–536. (Investigation of dirithromycin and erythromycylamine uptake by human neutrophils in vitro); Anderson R. et al. J. Antimicrob. Chemother. 1988, 22, 923–933. (An in-vitro evaluation of the cellular uptake and intraphagocytic bioactivity of clarithromycin (A-56268, TE-031), a new macrolide antimicrobial agent); Tasaka Y. et al. Jpn. J. Antibiot. 1988, 41, 836–840. (Rokitamycin uptake by alveolar macrophages); Harf R. et al. J. Antimicrob. Chemother. 1988, 22, 135–140. (Spiramycin uptake by alveolar macrophages), herein incorporated by reference in their entirety. U.S. Provisional Application 60/394,670 filed Jul. 8, 2002 and 60/395,190 filed Jul. 8, 2002 are herein incorporated by reference in their entirety describe macrolide linker complexes that have accumulating properties.

Moreover, the presence of accumulating property within immune system cells recruited to the site of inflammation, especially phagocytic cells can be easily ascertained by a person of ordinary skill in the field of the invention, using one of the well-known assays for this purpose. For example, the procedure detailed by Olsen, K. M. et al. *Anitmicrob. Agents & Chemother.* 1996, 40, 2582 can be used. Briefly, the cells to be tested, e.g., polymorphonuclear leukocytes can be obtained from venous blood of healthy volunteers by Ficoll-Hypaque centrifugation followed by 2% dextran sedimentation. Erythrocytes are removed by osmotic lysis, and PMN are evaluated by Trypan blue exclusion. Alternatively, other cell fractions can be separated and similarly tested. Tritiated macrolide compounds (e.g., 10 μM) are incubated with $2.5 \times 10^6$ cells for 120 minutes (37° C., 5% $CO_2$, 90% relative humidity) and the cells are subsequently removed from compound-containing supernatant by centrifugation e.g., through a silicon oil-paraffin layer (86 vol %: 14 vol %). The amount of compound is determined, e.g., by scintillation counting, and a score significantly elevated above background indicates accumulation of the macrolide in the cells being tested. See Bryskier et al. *Macrolides, Chemistry, Pharmacology and Clinical Use*; Arnette Blackwell: Paris, 1993 pp 375–386, at page 381, column 2, line 3. Alternatively, the compound is not radiolabeled but the amount of compound can be determined by HPLC.

Other assay methods that can be used are disclosed in Bryskier, A. J. et al. *Macrolides, Chemistry, Pharmacology and Clinical Use*; Arnette Blackwell: Paris, 1993 pp 375–386, incorporated by reference. See, in particular phagocytic uptake determination at pp 380–381 and the particular descriptions as to uptake and localization of macrolides at pp 381, 383 and 385 and the tables at 382 and 383.

In some preferred embodiments, this invention relates to compounds, their salts and solvates represented by the Formula I, wherein M specifically represents a 14- or 15-member lactonic ring macrolide subunit most preferably represented by the Formula II:

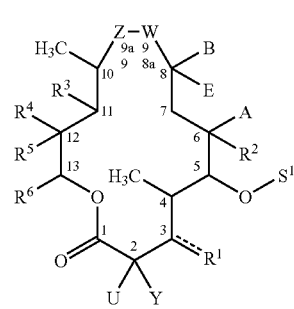

II wherein
(i) Z and W independently are

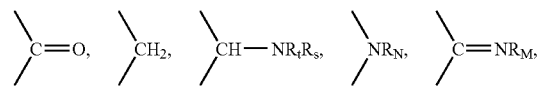

or a bond, wherein
$R_t$ and $R_s$ independently are H or alkyl (preferably methyl or H)
$R_M$ is OH, $OR^p$, alkoxy or substituted alkoxy (in either Syn or Anti configurations or mixtures thereof)
$R_N$ is H, $R^p$, alkyl, alkenyl, alkynyl, alkoxy, alkoxyalkyl or —C(=X)—$NR_tR_s$;
X is O or S;
provided that Z and W cannot both simultaneously be

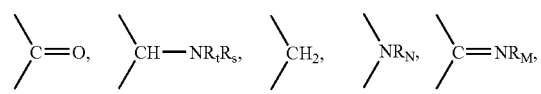

or a bond,
(ii) U and Y are independently H, halogen, alkyl, or hydroxyalkyl (preferably H, methyl, or hydroxymethyl);
(iii) $R^1$ is hydroxy $OR^p$, —O—$S^2$, or =O;
(iv) $S^1$ is a sugar moiety at position C/5 of the aglycone ring (e.g., a desozamine group) of the formula:

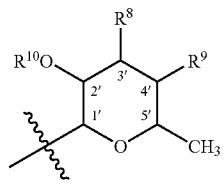

wherein
$R^8$ and $R^9$ are both hydrogen or together form a bond or $R^9$ is hydrogen and $R^8$ is —N($CH_3$)$R^y$, wherein $R^y$ may be $R^p$, $R^z$ or —C(O)$R^z$, wherein $R^z$ is hydrogen or cycloalkyl (preferably cyclohexyl) or alkyl (preferably a $C_1$–$C_7$ alkyl) or alkenyl (preferably $C_2$–$C_7$-alkenyl) or alkynyl (preferably $C_2$–$C_7$-alkynyl) aryl or heteroaryl or can be alkyl substituted with $C_1$–$C_7$ alkyl or $C_2$–$C_7$ alkenyl or $C_2$–$C_7$ alknyl or aryl or heteroaryl. ($R^y$ is preferably hydrogen, methyl, or ethyl);

$R^{10}$ is hydrogen or $R^p$;

(v) $S^2$ is a sugar moiety at position C/3 of the aglycone ring (e.g., a cladinosyl group) of the formula

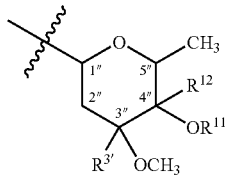

wherein $R^{3'}$ can be H or methyl and $R^{11}$ and $R^{12}$ are independently hydrogen, $R^{11}$ may be an $R^p$ or $R^{11}$ and $R^{12}$ together form a bond;

(vi) $R^2$ is H, hydroxy, $OR^p$ group, alkoxy (preferably $C_1$–$C_4$ alkoxy, most preferably methoxy), substituted alkoxy;

(vii) A is H or methyl;

(viii) B is methyl or epoxy;

(ix) E is H or halogen (preferably fluorine);

(x) $R^3$ is hydroxy, $OR^p$ group or alkoxy (preferably $C_1$–$C_4$ alkoxy, most preferably methoxy), substituted alkoxy or $R^3$ is a group that can combine with $R^5$ to form a "bridge" (e.g., a cyclic carbonate or carbamate) or if W or Z is

$R^3$ is a group that can combine with W or Z to form a "bridge" (e.g., a cyclic carbamate);

(xi) $R^4$ is $C_1$–$C_4$ alkyl (preferably methyl);

(xii) $R^5$ is H, hydroxy, $OR^p$ group, $C_1$–$C_4$ alkoxy, substituted alkoxy or a group that may combine with $R^3$ to form a bridge (e.g., a cyclic carbonate or carbamate);

(xiii) R is H or $C_1$–$C_4$ alkyl (preferably methyl or ethyl); wherein the subunit M has a linkage site through which it is linked to the subunit D via the linking group L, the linkage site being at one or more of the following:

a. any reactive hydroxy, N, or epoxy group located on $S^1$, $S^2$, or an aglycone oxygen if $S^2$ is (or if both $S^2$ and $S^1$ are) cleaved off;

b. a reactive >N—$R_N$, —$NR_rR_s$ or =O group located on Z or W;

c. a reactive hydroxy group located at any one of $R^1$, $R^2$, $R^3$, and $R^5$;

d. any other group that can be first derivatized to a hydroxy or —$NR_rR_s$ group and then linked to all or part of L (e.g., OH→=O→epoxy→

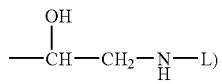

One or more $R^p$ groups may be independently present in the macrolide subunit of Formula II, wherein $R^p$ represents a protective group which may be selected from alkyl (preferably methyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl) group. The amino protecting groups may be removed by conventional techniques. Thus, for example acyl groups like alkanoyl, alkoxycarbonyl or aroyl may be removed by solvolysis, e.g. by hydrolysis under acidic or basic conditions. An arylmethoxycarbonyl group (benzyloxycarbonyl) may be cleaved by hydrogenolysis in the presence of a catalyst such as palladium-on-charcoal.

L can be selected to be a linking group represented by the Formula IV:

$$X^1—(CH_2)_m-Q-(CH_2)_n—X^2 \qquad IV$$

wherein $X^1$ is selected from: —$CH_2$—, —OC(=O)—, —C(=O), NO— or —OC(=O)NH—; —C(=O)NH—;

$X^2$ is selected from: —NH—, —$CH_2$—, —NHC(=O)— or —OC(=O)—, —C(=O), or —O

Q is —NH— or —$CH_2$— or absent;

wherein each —$CH_2$— or —NH— group may be optionally substituted by $C_1$–$C_7$-alkyl, $C_2$–$C_7$-alkenyl, $C_2$–$C_7$-alkynyl, C(O)$R^x$, C(O)O$R^x$, C(O)NH$R^x$ wherein $R^x$ may be $C_1$–$C_7$-alkyl, aryl or heteroaryl;

the symbols m and n independently are a whole number from 0 to 4 with the proviso that if Q=NH n cannot be zero

This definition of the linking group is preferred not only for hybrids of NSAIDs and macrolides of Formula II but for any conjugate within Formula I. Other linking groups can be used as long as they provide the necessary spacer and can serve to link one subunit of the Formula I with the other, as is well-known in the art. See, e.g., U.S. Pat. No. 6,297,260, which is incorporated by reference in its entirety, especially its claim 1 and the specific list of NSAIDs.

In Formula I, D represents a nonsteroidal anti-inflammatory subunit, i.e., a moiety of a nonsteroidal anti-inflammatory drug (NSAID). Suitable NSAIDs include, but are not limited to, those which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), and as inhibitors of both cyclooxygenase and lipoxygenase relates to nonsteroidal anti-inflammatory drug (NSAID), such as the commercially available NSAIDs aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAID compounds are disclosed in U.S. Pat. No. 6,297,260, incorporated entirely by reference (especially in the generic formulas of its claim 1 and the recitation of specific list of NSAID's contained therein and in claim 3, and thiazulidene NSAIDs disclosed in International Patent Application WO 01/87890, incorporated herein by reference in its entirety.

Preferred NSAIDs are acetyl salicylic acid, indomethacin, naproxen, ibuprofen, flurbiprofen, ketoprofen, sulindac, etodolac, ketorolac, suprofen, flunixin, sodium diclofenac, and tolmetin.

Bold-faced bonds in formulas contained herein denote bonds raised above the paper level; dash-drawn bonds denote bonds below the paper level, whereas broken lines represent a bond that may be either below or above the paper level. Parallel full and broken lines represent either a single or a double bond. Unless explicitly stated elsewhere herein, the following terms have the meanings ascribed to them below:

"Alkyl" means a linear or branched saturated monovalent hydrocarbon radical of one to ten carbon atoms, more preferably one to six carbon atoms The preferred straight-chain or branched-chain alkyls include methyl, ethyl, propyl, iso-propyl, butyl, sec-butyl and tert-butyl. Methyl is most preferred. Alkyl groups may be substituted with one up to five substituents including halogen (preferably fluorine or chlorine), hydroxy, alkoxy (preferably methoxy or ethoxy), acyl, acylamino cyano, amino, N—(C1–C4)alkyl amino (preferably N-methyl amino or N-ethylamino), N,N-di (C1–C4-alkyl)amino (preferably dimethylamino or diethylamino), aryl (preferably phenyl) or heteroaryl, thiocarbonylamino, acyloxy, amino, amidino, alkyl amidino, thioamidino, aminoacyl, aminocarbonylamino, aminothiocarbonylamino, aminocarbonyloxy, aryl, heteroaryl, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, cycloalkoxy, heteroaryloxy, heterocyclyloxy, and oxycarbonylamino. Such substituted alkyl groups are within the present definition of "alkyl." The present definition of alkyl carries over to other groups having an alkyl moiety such as alkoxy.

"Alkenyl" means a linear or branched monovalent hydrocarbon radical of two to ten and preferably two to six carbon atoms which has at least one double carbon-carbon bond. Alkenyl groups may be substituted with the same groups as alkyl and such optionally substituted alkenyl groups are encompassed within the term "alkenyl." Ethenyl, propenyl, butenyl and cyclohexenyl are preferred.

"Alkynyl" means a linear or branched monovalent hydrocarbon radical, having a straight-chain or a branched-chain of two to ten, and preferably two to six carbon atoms and containing at least one and preferably no more than three triple carbon-carbon bonds. Alkynyl groups can be substituted with the same groups as alkyl, and the substituted groups are within the present definition of alkynyl. Ethynyl, propynyl and butynyl groups are preferred.

"Cycloalkyl" means a cyclic group having 3–8 carbon atoms having a single ring optionally fused to an aryl or heteroaryl group. The cycloalkyl groups can be substituted as specified for "aryl" below, and the substituted cycloalkyl groups are within the present definition of "cycloalkyl". Preferred cycloalkyls are cyclopentyl and cyclohexyl.

"Aryl" means an unsaturated aromatic carbocyclic group having 6–14 carbon atoms having a single ring such as phenyl or multiple fused rings such as naphthyl. Aryl may optionally be further fused to an aliphatic or aryl group or can be substituted with one or more substituents such as halogen (fluorine, chlorine and/or bromine), hydroxy, $C_1$–$C_7$ alkyl, $C_1$–$C_7$ alkoxy or aryloxy, $C_1$–$C_7$ alkylthio or arylthio, alkylsulfonyl, cyano or primary or nonprimary amino.

"Heteroaryl" means a monocyclic or a bicyclic aromatic hydrocarbon ring having from 2 to 10 carbon atoms and from 1 to 4 heteroatoms, such as O, S or N. The heteroaryl ring may optionally be fused to another heteroaryl, aryl or aliphatic cyclic group. Examples of this type are furan, thiophene, pyrrole, imidazole, indole, pyridine, oxazole, thiazole, pyrrole, pyrazole, tetrazole, pyrimidine, pyrazine and triazine, with furan, pyrrole, pyridine and indole being preferred. The term includes groups that are substituted with the same substituents as specified for aryl above.

"Heterocyclic" means a saturated or unsaturated group having a single or multiple rings and from 1 to 10 carbon atoms and from 1–4 heteroatoms selected from nitrogen, sulphur or oxygen, wherein in a fused ring system the other ring or rings can be aryl or heteroaryl. Heterocyclic groups can be substituted as specified for alkyl groups and the thus substituted heterocyclic groups are within the present definition.

The present invention also encompasses pharmaceutically acceptable salts of the present compounds. Pharmaceutically suitable salts of the compounds of the present invention include salts with inorganic acids (e.g. hydrochloric, hydrobromic, phosphoric, metaphosphoric, nitric or sulfuric acid) or organic acids (e.g. tartaric, acetic, methane-sulfonic, trifluoroacetic, citric, maleic, lactic, fumaric, benzoic, succinic, methanesulfonic, oxalic and p-toluenesulfonic acids).

The present invention also encompasses prodrugs of the Formula I compounds, i.e., compounds which release an active parent drug according to Formula (I) in vivo when administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or carboxy group of a Formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of Formula I, or any other derivative which upon being brought to the physiological pH or through enzyme action is converted to the active parent drug.

The present invention also encompasses solvates (preferably hydrates) of the compounds of Formula I or their salts.

The compounds of the Formula I have one or more chirality centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". The present invention encompasses all individual isomers of compounds of Formula I. The description or naming of a particular compound in the specification and claims is intended to include both individual enantiomers and mixtures, racemic or otherwise, thereof. Methods for the determination of stereochemistry and the resolution of stereoisomers are well-known in the art.

The present invention also encompasses stereoisomers of the syn-anti type, and mixtures thereof encountered when an oxime or similar group is present. The group of highest Cahn Ingold Prelog priority attached to one of the terminal doubly bonded atoms of the oxime, is compared with hydroxyl group of the oxime. The stereoisomer is designated as Z (zusammen=together) or Syn if the oxime hydroxyl lies on the same side of a reference plane passing through the C=N double bond as the group of highest priority; the other stereoisomer is designated as E (entgegen=opposite) or Anti.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The benefit to a subject to be treated is either statically significant or at least perceptible to the patient or to the physician A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature. Swelling, and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing;

other allergy disorders, such as allergic rhinitis—sneezing, itching, runny nose conditions associated with acute trauma such as cerebral injury following stroke—sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis;

other inflammatory conditions associated with particular organs or tissues, such as nephritis (e.g., glomerulonephritis)-oliguria, abnormal urinalysis;

inflamed appendix—fever, pain, tenderness, leukocytosis;

gout—pain, tenderness, swelling and erythema of the involved joint, elevated serum and/or urinary uric acid;

inflamed gall bladder—abdominal pain and tenderness, fever, nausea, leukocytosis;

chronic obstructive pulmonary disease—shortness of breath, wheezing;

congestive heart failure—shortness of breath, rales, peripheral edema;

Type II diabetes—end organ complications including cardiovascular, ocular, renal, and peripheral vascular disease lung fibrosis—hyperventilation, shortness of breath, decreased oxygenation;

vascular disease, such as atherosclerosis and restenosis—pain, loss of sensation, diminished pulses, loss of function and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

Preferably, in the compounds represented by the Formula II,

Z and W together are —N($R_N$)C(O)—, —C(O)N($R_N$)—, >C—$NR_sR_t$, —C(O)—, >C=N—$R_M$, —$CH_2NR_N$— or —$NR_NCH_2$—, most preferably, —$NCH_3CH_2$—, —$NHCH_2$—, —$CH_2NH$—, —C(O)NH, —NHCO—, $R_s$, $R_t$ is methyl or H;

$R_M$ is OH or methoxy;

X is O;

$R_N$ is H, methyl, or —C(=X)—$NR_tR_s$;

A is H or methyl

U, Y are H, F, methyl or hydroxymethyl;

$R^1$ is hydroxy, —O—$S^2$, or =O $R^2$ is H, hydroxy or methoxy;

$R^3$ is OH, methoxy or a group that forms a cyclic carbamate bridge with W or Z;

$R^4$ is methyl;

$R^5$ is H, OH, methoxy or a group that forms a cyclic carbonate or carbamate bridge with $R^3$;

The linkage is through the nitrogen of Z at N/9a or N/8a positions or through the carbon of $R^{12}$ or through the oxygen of $R^{11}$ both at C/4" position of $S^2$ sugar.

$R^6$ is H, methyl or ethyl;

$R^8$ is H, N($CH_3$)$_2$, NH($CH_3$) or N($CH_3$)$CH_2CH_3$, $R^9$ is H

The linkage site is preferably at position C/3; or through the amino group at position C/3' of $S^1$ sugar or at position C/11 or at W or Z, or through position C/4" of $S^2$ sugar.

Also preferred are compounds within Formula I wherein M is of Formula II and (i) Z is $NCH_3$, W is $CH_2$, $R^2$ is hydroxy; or (ii) Z is NH, W is =CO, and $R^2$ is methoxy. (The compounds described in this paragraph may or may not satisfy the remaining foregoing preferences in the immediately preceding section, but preferably they do.)

A further aspect of the present invention relates to processes for the preparation of compounds represented by Formula I. Generally, the compounds of Formula I may be obtained in the following way: one end of the chain L is first linked to the macrolide subunit M, and then the other end of the chain is linked to the nonsteroid subunit D; or, one end of the chain L is first linked to the nonsteroidal anti-inflammatory subunit D and then the other end of the chain to the macrolide subunit M, or finally, one moiety of the chain is linked to the macrolide subunit M, whereas the other moiety of the chain is linked to the nonsteroid subunit D, with the ends of the chain parts being then chemically linked to form the chain L.

It will be appreciated by those skilled in the art that it may be desirable to use protected derivatives of intermediates used in the preparation of the compounds of Formula I. Protection and deprotection of functional groups may be performed by methods known in the art. Hydroxyl or amino groups may be protected with any hydroxyl or amino protecting group, for example, as described in Green T. W.; Wuts P. G. M. *Protective Groups in Organic Synthesis*: John Wiley and Sons, New York, 1999. The amino protecting groups may be removed by conventional techniques. For example, acyl groups, such as alkanoyl, alkoxycarbonyl and aroyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

More specifically, compounds within Formula I can be prepared by the following processes.

a) Compounds of Formula I, where $X^2$ is —NH—, can be formed by reacting a nonsteroidal anti-inflammatory subunit represented by Formula V:

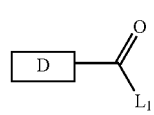

V wherein $L_1$ represents a leaving group (such as hydroxy), and a free amino group of a macrolide subunit represented by Formula VIa:

VIa

The reaction is generally performed with acid derivatives which have the ability to activate the carboxylic acid group of the nonsteroidal anti-inflammatory subunit, such as halogenides, mixed anhydrides and especially carbodiimides (such as -(3-dimethylaminopropyl)-3-ethyl-carbodiimide (EDC) and benzotriazoles). The reaction proceeds in the presence of a base, such as an organic base (e.g., triethylamine), at room temperature and under an inert atmosphere, such as nitrogen or argon. The reaction may require several hours to several days to come to completion.

Nonsteroidal anti-inflammatory subunits represented by Formula V are commercially available. The non-steroidal anti-inflammatory subunit D may contain a —C(O)$L^1$ group (such as a free carboxylic acid group) or be derivatized by methods known in the art.

Scheme I

NSAID—OH + SUCCINIC ANHYDRIDE $\xrightarrow[\text{CH}_2\text{Cl}_2]{\begin{array}{c}1.\ \text{Pyr}\\2.\ \text{NEt}_3,\ 4\text{-PP,}\end{array}}$ NSAID—OC(O)CH$_2$CH$_2$COOH According to Scheme I, NSAID compounds having a hydroxyl group may alternatively be derivatized by the action of succinic anhydride in the presence of pyridine followed by reaction of the intermediate so produced with triethylamine, 4-pyrrolopyridine in methylene chloride to produce NSAID having free carboxylic acid group (Huang C. M. et al. Chem.&Biol. 2000, 7, 453–461, Hess S. et al. Bioorg.&Med. Chem. 2001, 9, 1279–1291) The NSAID derivatives so produced may be coupled either to a linker macrolide compound such as formula VIa or directly to a macrolide.

Scheme II

NSAID>NH $\xrightarrow[\text{tert-butyliodoacetate}]{\text{NaH, DMF}}$ NSAID>N—CH$_2$—C(O)—O—C(CH$_3$)$_3$ ↓ TFA, CH$_2$Cl$_2$

NSAID>NCH$_2$COOH

According to Scheme II, NSAID compounds having an amino group may alternatively be derivatized by the action of sodium hydride and tert-butyliodoacetate in N,N-dimethylformamide to produce a (butoxy carbonyl derivative of the NSAID which is then reacted with (trifluoracetic acid in methylene chloride to produce NSAID having free carboxylic acid group (Hess S. et al. Bioorg.&Med. Chem. 2001, 9, 1279–1291). The NSAID derivatives so produced may be coupled either to a linker macrolide compound such as formula VIa or directly to a macrolide.

Scheme III

NSAID—NH$_2$ + SUCCINIC ANHYDRIDE $\xrightarrow[\text{DIPEA, DMF}]{\text{DMAP}}$ NSAID—NHC(O)CH$_2$CH$_2$COOH Alternatively by NSAID compounds having an amino group may be derivatized according to Scheme III by the action of succinic anhydride in the presence of dimethylaminopyridine, N,N'-diisopropylethylamine in dimethylformamide to produce NSAID having free carboxylic acid group (Pandori M. W. et al. Chem.&Biol. 2002, 9, 567–573). The NSAID derivatives so produced may be coupled either to a linker macrolide compound such as formula VIa or directly to a macrolide.

Preparation of the starting macrolide subunits of the structure VIa has been described in PCT/HR02/00001, incorporated by reference in its entirety copy attached as Appendix 1. See also Bright, U.S. Pat. No. 4,474,768 and Bright, G. M. et al. *J. Antibiot.* 1988, 41, 1029–1047. each incorporated by reference in its entirety.

For example, when L is —K—NH— (wherein K is the portion of the linking molecule L attached to the macrolide) the compound of Formula I can be formed by derivatizing an >NH group on the macrolide ring to an >N—K—NH$_2$ group and reacting the derivatized macrolide with a nonsteroid anti-inflammatory subunit represented by Formula V; wherein L$^1$ is a leaving group according to Scheme IV.

Scheme IV

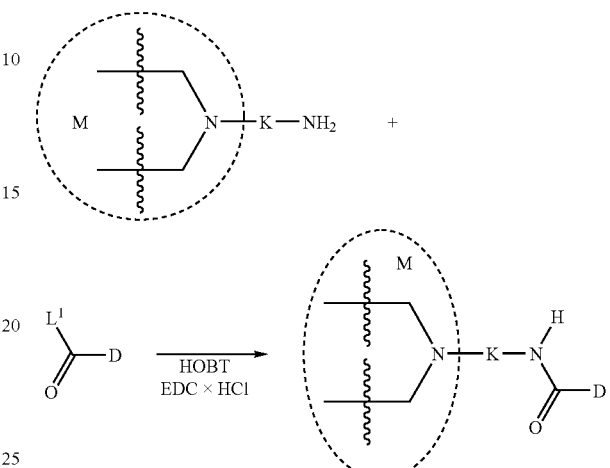

This process may also be performed when the NH group in the macrolide is attached at the 3' position of a sugar ring S$^1$ (i.e., a desozamine sugar) of the macrolide according to Scheme IV:

Scheme V or the 4" position of the sugar ring S$^2$ according to Scheme VI:

Scheme VI

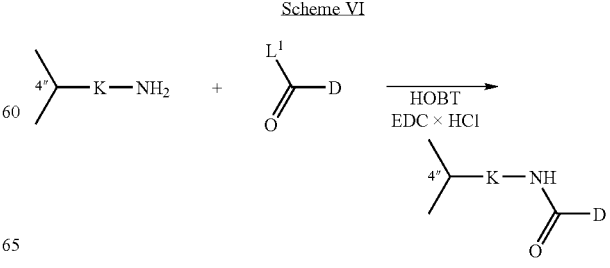

The reactant macrolide subunit can be formed by oxidizing the corresponding macrolide having a hydroxy substituent at the 4" position on cladinose sugar to obtain a =O substituent at the 4" position, converting the

at the 4" position to an epoxy group

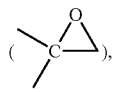

and cleaving the epoxy group with an appropriate reactant(s) to yield the reactant macrolide subunit (M-CH$_2$—NH—K—NH$_2$).

b) Compounds represented by Formula I, where X$^2$ is —OC(O)—, can be formed by reacting a nonsteroidal anti-inflammatory subunit represented by Formula V and the free hydroxyl group of a macrolide subunit represented by Formula VIb:

VIb

The reaction is generally performed with acid derivatives which have the ability to activate the carboxylic acid group of the nonsteroidal anti-inflammatory subunit, such as halogenides (such as ethylene dichloride (EDC), mixed anhydrides, especially carbodiimides. The reaction is typically performed at room temperature under an inert atmosphere, such as nitrogen or argon. The reaction may require several hours to several days to come to completion.

The starting macrolide subunits of the structure VIb are known compounds or may be obtained according to the procedures described for analogous compounds, such as those described in Costa A. M. et al. *Tetrahedron Letters* 2000, 41, 3371–3375, which is hereby incorporated by reference.

For example, when linkage L is —K—O—, the compound of Formula I can be formed by (1) derivatizing an >NH group on a macrolide to an >N—K—OH group and (2) reacting the derivatized macrolide with the free carboxylic acid group on a non-steroidal anti-inflammatory subunit D according to Scheme VII:

Scheme VII

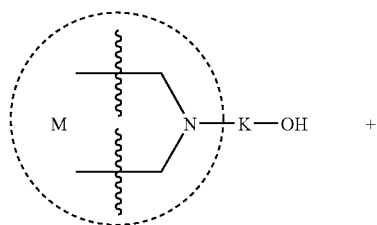

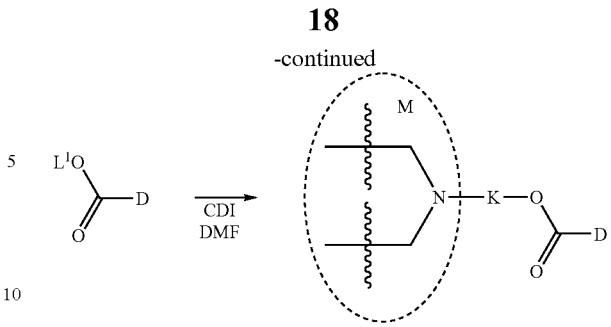

The linkage group —K—OH can be attached to the primary or secondary nitrogen atom of the macrolide subunit as follows. The macrolide subunit is reacted with an alkenoyl derivative, such as CH$_2$=CH(CH$_2$)$_m$C(O)O-Alkyl (e.g., methylacrylate). The ester group (i.e., —C(O)O-Alkyl) is then reduced, such as with a metal hydride (e.g., LiAlH$_4$) in an anhydrous organic solvent, to yield the macrolide subunit having the linkage group —K—OH (i.e., M-K—OH). The reduction is typically performed at a low temperature and preferably at 0° C. or lower.

This process can also be performed when the NH group is attached at the 3' position of a sugar ring in the macrolide (such as a sugar at the 5 position of the macrolide).

c) Compounds represented by Formula I, wherein X$^1$ is —OC(O)—, Q is —CH$_2$— or NH, and X$^2$ is —NH—, can be prepared by reacting a macrolide subunit represented by the formula

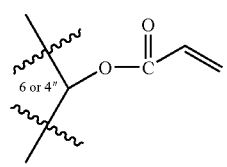

where 4" is the 4 position on a sugar S$^2$, such as a cladinose sugar, and a derivatized nonsteroidal anti-inflammatory subunit having a free amino group represented by the formula:

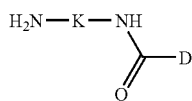

in a solvent, such as acetonitrile, to yield

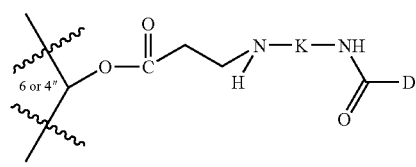

The derivatized nonsteroidal anti-inflammatory subunit (i.e., D-C(O)—NH—K—NH$_2$) may be formed by reacting an appropriate amine (having the linkage group —K—NH$_2$) with a carboxylic acid group of a nonsteroid anti-inflammatory drug.

d) Compounds represented by Formula I, where X$^1$ is —OC(O)NH— and X$^2$ is —NH—, can be prepared by reacting a macrolide subunit and a derivatized nonsteroidal anti-inflammatory subunit having a free amino group as shown below.

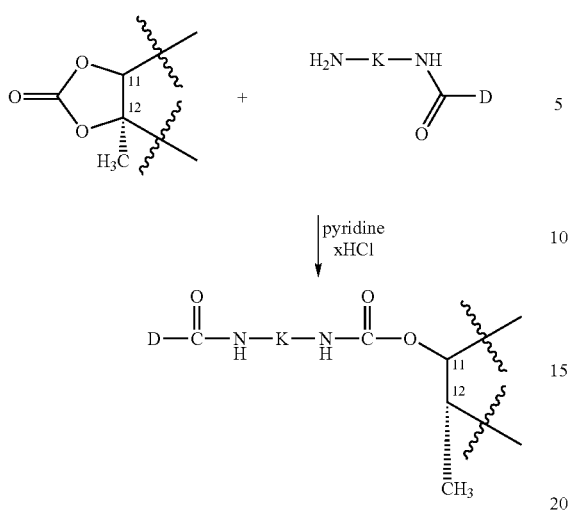

e) Compounds represented by Formula I, where $X^1$ is —OC(O)NH— and $X^2$ is —NH—, can be also prepared by reacting a macrolide subunit and a nonsteroidal anti-inflammatory subunit having a free carboxylic acid group as shown below.

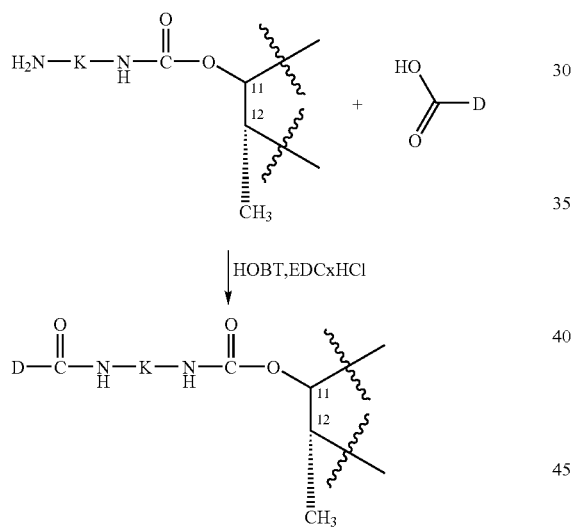

f) The compounds of the Formula I can be prepared by reacting a macrolide subunit having a leaving group $L^2$ (such as Br), and a non-steroidal anti-inflammatory drug as shown below.

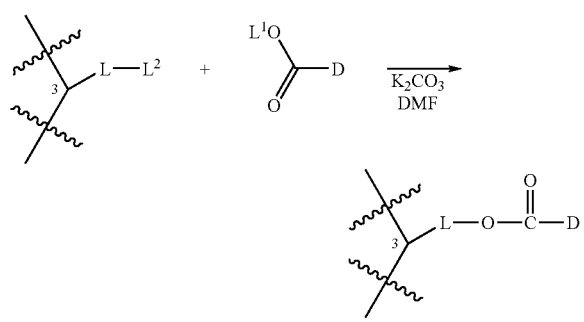

The starting macrolide subunit can be prepared by cleaving the sugar group attached at the 3-position of the macrolide ring and then reacting the macrolide with a reagent of the Formula $L^2$-L-$L^1$, where $L^2$ is a leaving group.

g) The compounds of Formula I can be prepared by reacting a macrolide subunit having a leaving group $L^2$ (such as Br), and a non-steroidal anti-inflammatory drug as shown below.

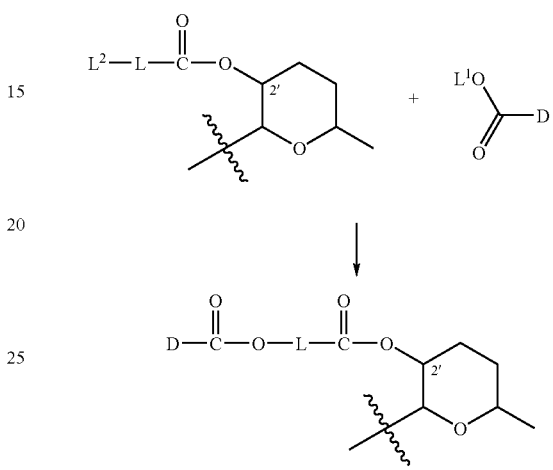

h) Compounds of the Formula I can be prepared by reacting a macrolide subunit having a leaving group $L^2$ (such as Br) and a non-steroidal anti-inflammatory drug as shown below.

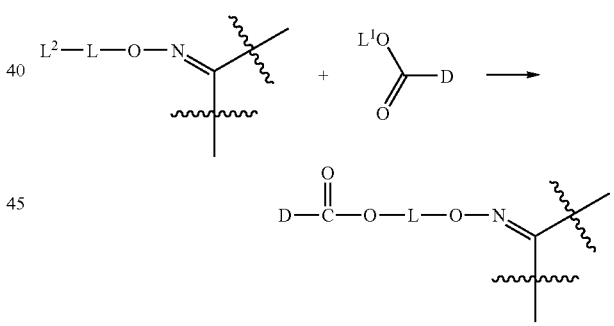

The 16-membered ring macrolides are traditionally divided into sub-families based upon the substitution patterns of their aglycones. The principal prototypes of this family can be represented by leucomycin, spiramycin and tylosin.

Tylosin is a representative of 16-membered macrolides, which possesses a highly substituted aglycone with two double bonds (tylonolide) and a third saccharide substituent (β-D-mycinose) beta-D-mycosine in addition to the disaccharide attached to the 5-hydroxyl group. Hydrolysis of mycarose from disaccharide yielded desmycarosyl-tylosin (desmycosin).

Potential Sites of Modification in Desmycosin:
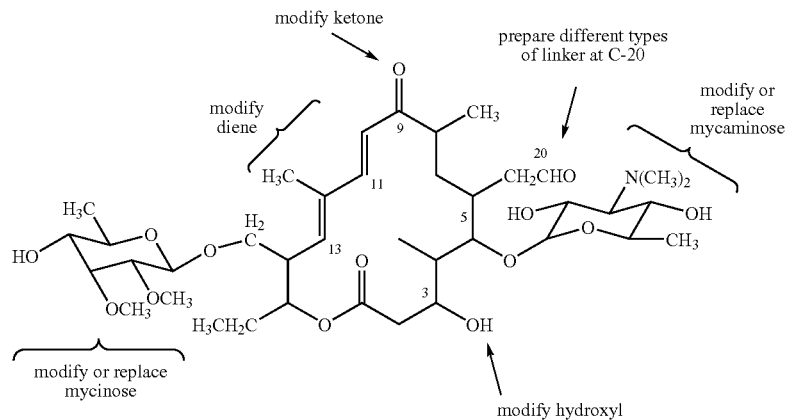

For example, a 16-membered ring macrolide hybrid could be prepared by reductive amination of the C-20 aldehyde group.

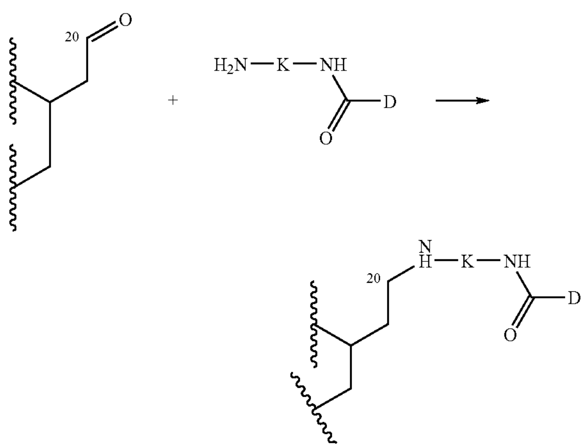

This reaction could be used also for 17-membered azalides like 8a-aza-homodesmycosins and its derivatives (such as di- and tetrahydro derivatives).

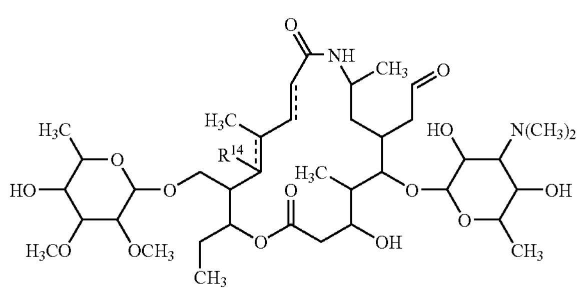

$R^{14}$ is hydrogen or hydroxy

The other possibilities in 16-membered ring macrolide derivatisation are transformations of double bonds by epoxidation, and cleaving the epoxy group with an appropriate reactant (such as diamines) to yield the reactant macrolide subunit (M-$CH_2$—NH—K—$NH_2$).

Also the ketone in position 9 can be modified by hydroxylamine hydrochloride to yield oxime and then reduced to amine.

A further aspect of the present invention relates to the use of compounds of Formula I in the treatment of inflammatory diseases, disorders and conditions characterized by or associated with an undesirable inflammatory immune response, especially of all diseases and conditions induced by or associated with an excessive secretion of TNF-α and IL-1.

A therapeutically effective amount of the compound of the present invention can be determined by methods known in the art. Since the compound of the present invention is more efficiently delivered to the desired site than the corresponding nonsteroidal anti-inflammatory drug alone, a lesser amount of the compound on a molar basis than of the nonsteroidal anti-inflammatory drug can be administered while still achieving the same therapeutic effect. Furthermore, since administration of the compound results in fewer side effects than with the corresponding nonsteroidal anti-inflammatory drug, the NSAID amount can be increased. Thus, the table below serves only as a guide. A threshold therapeutically effective amount of the compound, a pharmaceutically acceptable salt thereof, a solvate thereof, or a prodrug thereof is generally equal to or less than a therapeutically effective amount of the nonsteroidal anti-inflammatory drug on a molar basis. Broad and preferred effective amounts of the compound, a pharmaceutically salt thereof, a solvate thereof, or a prodrug thereof are shown in the table below.

| | Amount of Compound, Pharmaceutically Salt Thereof, Solvate Thereof, or Prodrug Thereof | |
|---|---|---|
| | mg/kg body weight/day of the NSAID (had it been administered alone | μmol/kg body weight/day of the hybrid or the (NSAID) |
| Broad | from about 0.001 to about 1000 | from about 0.004 to about 4000 |
| Preferred | from about .01 to about 100 | from about 0.04 to about 400 |
| More Preferred | from about 1 to about 100 | from about 4 to about 400 |
| Most Preferred | from about 3 to about 30 | from about 12 to about 120 |

Thus, for example, the preferred dosage range for indomethacin is 50–200 mg/day, which corresponds to the range of 140 to 560 μmol per day. The same mole-based range, 140–560 mol of a hybrid compound of the invention, will be the starting point for determining the preferred dosage range. Refinements of this approach are well within the skill of the art.

Further, the present invention relates to pharmaceutical compositions containing an effective dose of compounds of the present invention as well as pharmaceutically acceptable excipients, such as carriers or diluents.

The preparation of the pharmaceutical compositions of the invention can include mixing, granulating, tabletting and dissolving the ingredients. Chemical carriers can be in solid or liquid form. Solid carriers can be lactose, sucrose, talc, gelatine, agar, pectin, magnesium stearate, fatty acids without limitation. Liquid carriers can be syrups, oils such as olive, sunflower seed or soybean oils, water, or physiologic saline without limitation. Similarly, carriers may also contain a component for a sustained release of the active component such as glyceryl monostearate or glyceryl distearate. Several forms of pharmaceutical compositions can be prepared. If a solid carrier is used, these forms can include tablets, caplets, solid gelatinous capsules, powders or granules without limitation that can be administered orally. The amount of the solid carrier can vary but mainly it is in the range from 25 mg to 1 g. If a liquid carrier is used, the formulation can be in the form of a syrup, emulsion, soft gelatinous capsules, or sterile injectable liquids, or nonaqueous liquid suspensions.

The compounds of the present invention can be administered topically or systemically, e.g., orally, parenterally, percutaneously, mucosally, e.g., buccally, intranasally, intrarectally and intravaginally. "Parenterally" means by intravenous, intramuscular or subcutaneous route. The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, nonregulated, or dysregulated) inflammatory immune response involving the production of inflammatory cytokines or other inflammation mediators, including without limitation TNF-α and IL-1β. They include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar UV sources); inflammatory bowel disease, such as Crohn's disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection.

Efficacy of the present compounds can be assessed by any method for assessing inflammation or anti-inflammatory effect. There are many known methods for this purpose including without limitation, use of contrast ultrasound in conjunction with injection of microbubbles, measurement of inflammatory cytokines (such as TNF-α, IL-1, IFN-γ) measurement of activated immune system cells as well as observation (reduction of oedema, reduction of erythema, reduction of pruritus or burning sensation, reduction of body temperature, improvement in function of the afflicted organ) as well as any of the methods provided below.

The therapeutic effect of compounds of the present invention was determined in in vitro and in vivo experiments such as the following.

Determination of TNF-α and IL-1β Secretion in Mononuclear Cells of Human Peripheral Blood In Vitro Peripheral blood mononuclear cells (PMBC) were prepared from heparinized whole blood after separation of PMBC on Ficoll-Hypaque (Amersham-Pharmacia). For the determination of TNF-α level, $3.5–5\times10^4$ cells were cultured in a total volume of 200 µl within a period of 18 to 24 hours on microtiter flat bottom plates (96 wells, Falcon) in RPMI 1640 medium supplemented with 10% of heat-inactivated human AB serum (Croatian Centre For Transfusion Medicine, Zagreb), 100 units/mL of penicillin, 100 mg/mL of streptomycin and 20 mM HEPES (Invitrogen Life Technologies). The cells were incubated at 37° C. in an atmosphere with 5% $CO_2$ and 90% moisture. The cells in a negative control were cultured only in the medium (NC), while the secretion of TNF-α in a positive control was stimulated by the addition of 1 µg/mL lipopolysaccharide (LPS, E. coli serotype 0111:B4, SIGMA) (PC) and the effect of the tested substances on TNF-α secretion was tested after their addition to cell cultures stimulated with LPS (TS). The TNF-α level in the cell supernatant was determined by ELISA according to the manufacturer's (R&D Systems) suggestions. The test sensitivity was <3 pg/mL TNF-α. The determination of IL-1β level was performed as described for TNF-α determination, only that $1\times10^5$ cells/well and 0.1 ng/mL of LPS were used. IL-1β level was determined by ELISA (R&D Systems). The percentage inhibition of TNF-α or IL-1β production was calculated by the following equation:

$$\% \text{ inhibition}=[1-(TS-NC)/(PC-NC)]\times 100$$

IC-50 value was defined as the concentration of the substance at which 50% of TNF-α production was inhibited. The compounds demonstrating IC-50 in concentrations of 20 µM or lower were considered active. IC-50 was calculated using Graph Pad Prism Software.

Determination of TNF-α Secretion by RAW 264.7 Cells

The cells were grown in 10% fetal bovine serum (FBS) in DMEM medium (Invitrogen Life Technologies) at 37° C. in an atmosphere with 5% $CO_2$ and 90% moisture. 20 000 cells/well were plated in 96 well plate (Falcon). The cells in a negative control were cultured only in the medium (NC), while the secretion of TNF-α in a positive control was stimulated by the addition of 500 pg/mL lipopolysaccharide (LPS, E. coli serotype 0111:B4, SIGMA) (PC) and the effect of the tested substances on TNF-α secretion was tested after their addition to cell cultures stimulated with LPS (TS). The TNF-α level in the cell supernatant was determined by ELISA according to manufacturer's (R&D Systems, Biosource) suggestions. The percentage inhibition of TNF-α production was calculated by the following equation:

$$\% \text{ inhibition}=[1-(TS-NC)/(PC-NC)]\times 100$$

IC-50 value was defined as the concentration of the substance at which 50% of TNFα production was inhibited. The compounds demonstrating IC-50 in concentrations of 10 μM or lower were considered active.

Human Prostaglandin-H Synthase—1 (hPGH-1) and Human Prostaglandin-H Synthase—2 (hPGH-2) Inhibition Assay Genes coding hPGH-1 and hPGH-2 were amplified with PCR using Platinum pfx DNA polymerase (Invitrogen Life Technologies) from human placenta cDNA library (Stratagene). Primer sequences used for hPGH-1 are:

5' atataagcttgcgccatgagccggagtcttc 3' (SEQ ID NO: 1) and

5' atatggatcctcagagctctgtggatggtcgc 3' (SEQ ID NO: 2); for hPGH-2

5' atataagcttgctgcgatgctcgcccgc 3' (SEQ ID NO: 3) and

5' atatggatccctacagttcagttcagtcgaacgttc 3' (SEQ ID NO: 4).

PCR products were cloned into HindIII and BamHI restriction sites of pcDNA3.1 (Hygro(+) plasmid (Invitrogen Life Technologies), sequences were confirmed by sequencing.

Transfection was performed on COS-7 cells (ATCC), cells were grown in 10% foetal bovine serum (FBS) in DMEM medium (Invitrogen Life Tecnologies), 37° C. in an atmosphere with 5% $CO_2$ and 90% moisture, to full confluency in 24 well plate (Falcon). 1 μg plasmid DNA (pcDNA Hygro 3.1 (+) containing PGH-1 or PGH-2 gene, or pcDNA Hygro 3.1 (+) for negative control samples) was combined with 1,5 μl Lipofectamine 2000 (Invitrogen Life Technologies), following manufacturer's recommendations. 24–48 hours post transfection, tested compounds in DMEM were added to cells without medium removal, and after 40 minutes, arachidonic acid (Sigma) was added to final 20 μM concentration. After 30 minutes supernatants were removed and PGE-2 was measured with PGE-2 assay kit (Cayman) following manufacturer's instructions. No production of PGE-2 was detected in negative control.

% inhibition was calculated by the following equation:

% inhibition=(1−sample PGE-2 concentration/positive control PGE-2 concentration)*100

In Vivo Model of LPS-Induced Exccessive Secretion of TNF-α in Mice

TNF-α secretion in mice was induced according to the previously described method (Badger A. M. Et al., *J. of Pharmac. and Env. Therap.* 279 1996 1453–1461). In the test, male BALB/c mice at an age of 8 to 12 weeks in groups of 6 to 10 animals were used. Animals were treated p.o. either only with the solvent (in a negative and a positive control) or with solutions of the substance 30 minutes prior to the i.p. treatment with LPS (*E. coli* serotype 0111:B4, Sigma) in a dose of 25 μg/animal. Two hours later the animals were euthanized by means of i.p. injection of Roumpun (Bayer) and Ketanest (Park-Davis). A blood sample from each animal was collected in a "vacutaner" tube (Becton Dickinson) and the plasma was separated according to the manufacturer's suggestions. The TNF-α level in the plasma was determined by ELISA (Biosource, R&D Systems) according to the process prescribed by the manufacturer. The test sensitivity was <3 pg/mL TNF-α. The percentage inhibition of TNF-α production was calculated by the following equation:

% inhibition=[1−(TS—NC)/(PC—NC)]*100

The compounds demonstrating a 30% or higher inhibition of TNF-α production at a dose of 10 mg/kg were considered active.

Representative results expressed qualitatively are set forth below for four of the foregoing tests, and for three of the compounds exemplified below:

| Compound | TNF-α PBMC $IC_{50}$ | hPGH-1 $IC_{50}$ | hPGH-2 $IC_{50}$ | LPS induced excessive secretion of TNF-α % of inhibition |
|---|---|---|---|---|
| S-(+)-Ibuprofen | >30 μM | 0.5 μM | 0.8 μM | ND |
| Ex. 4 | 1 μM | >30 μM | 1 μM | 70 |
| Ex. 5 | 1 μM | 10 μM | 10 μM | 66 |
| Ex. 10 | 10 μM | >30 μM | >30 μM | 47 |

ND—not determinated

Writhing Test for Analgesic Activity

In this test, pain is induced with an injection of an irritant, usually acetic acid, into the peritoneal cavity of mice. The animals respond by the characteristic writhings, which gave the name of the test (Collier H. O. J. et al. *Pharmac. Chemother.* 1968, 32, 295–310; Fukawa K. et al. *J. Pharmacol. Meth.*, 1980, 4, 251–259; Schweizer A. et al. *Agents Actions*, 1988, 23, 29–31). This test is suitable for the determination of analgetic activity of compounds. Process: male BALB-/c mice (Charles River, Italy) at an age of 8 to 12 weeks were used. Methyl cellulose was administered p.o. to a control group, 30 minutes prior to i.p. administration of acetic acid in a concentration of 0.6%, whereas to the test groups a standard (acetyl salicylic acid) or test substances in methylcellulose were administered p.o. 30 minutes prior to i.p. administration of 0.6% acetic acid (volume 0.1 mL/10 g). Mice were individually placed under glass funnels and the number of writhings of each animal was recorded during a period of 20 minutes. The percentage inhibition of writhings was calculated according to the equation:

% inhibition=(mean value of number of writhings in the control group−number of writhings in the test group)/number of writhings in the control group×100.

The compounds demonstrating the same or better analgesic activity than acetyl salicylic acid were considered active.

In Vivo Model of LPS-Induced Shock in Mice

Male BALB/c mice at an age of 8 to 12 weeks (Charles River, Italy) were used. LPS isolated from Serratie marcessans (Sigma, L-6136) was diluted in sterile saline. The first LPS injection was administered intradermally in a dose of 4 μg/mouse. 18 to 24 hours later LPS was administered i.v. in a dose of 200 μg/mouse. To a control group, two LPS injections were administered in the above described manner. The test groups were administered the substances p.o. half an hour prior to each LPS administration. The survival after 24 hours was observed.

The compounds resulting in a 40% or better survival at a dose of 30 mg/kg were considered active.

The compounds of Examples 1–12 demonstrate activity in at least two investigated tests. These results, however, only illustrate the biological activity of the compounds and do not limit the present invention in any way.

Preparation Processes with Examples
Precursors
Nonsteroidal Anti-Inflammatory Subunits

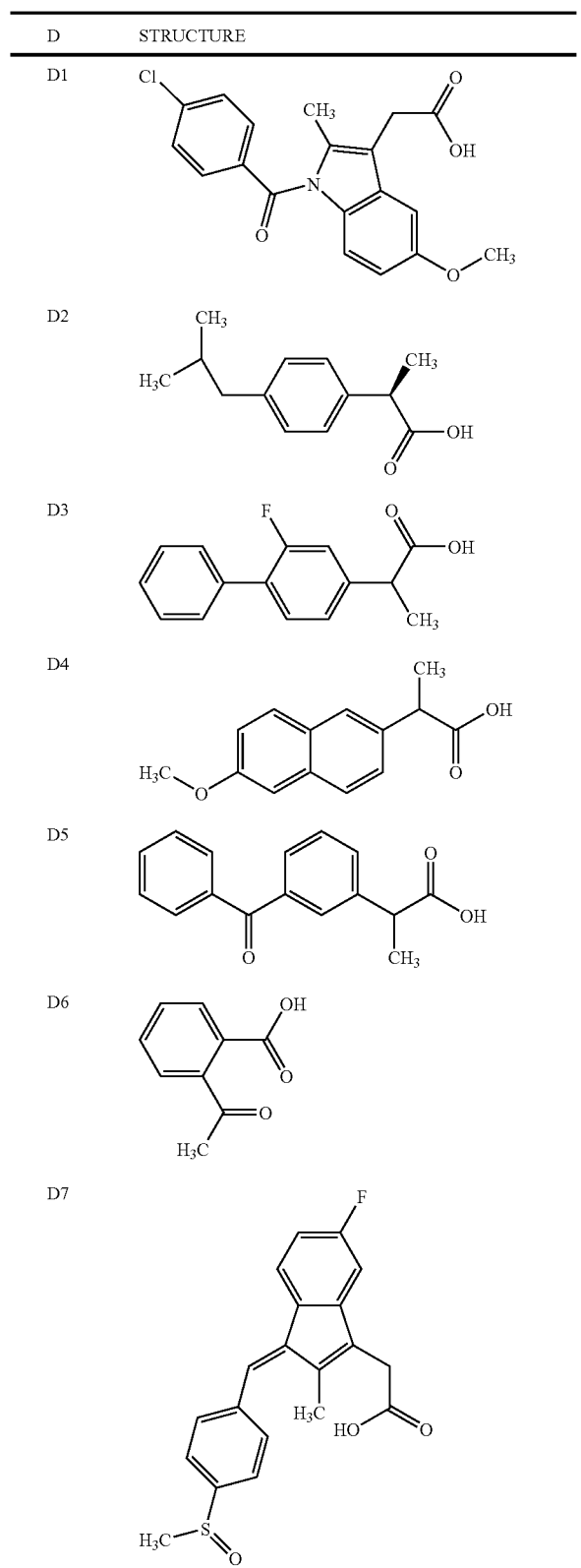

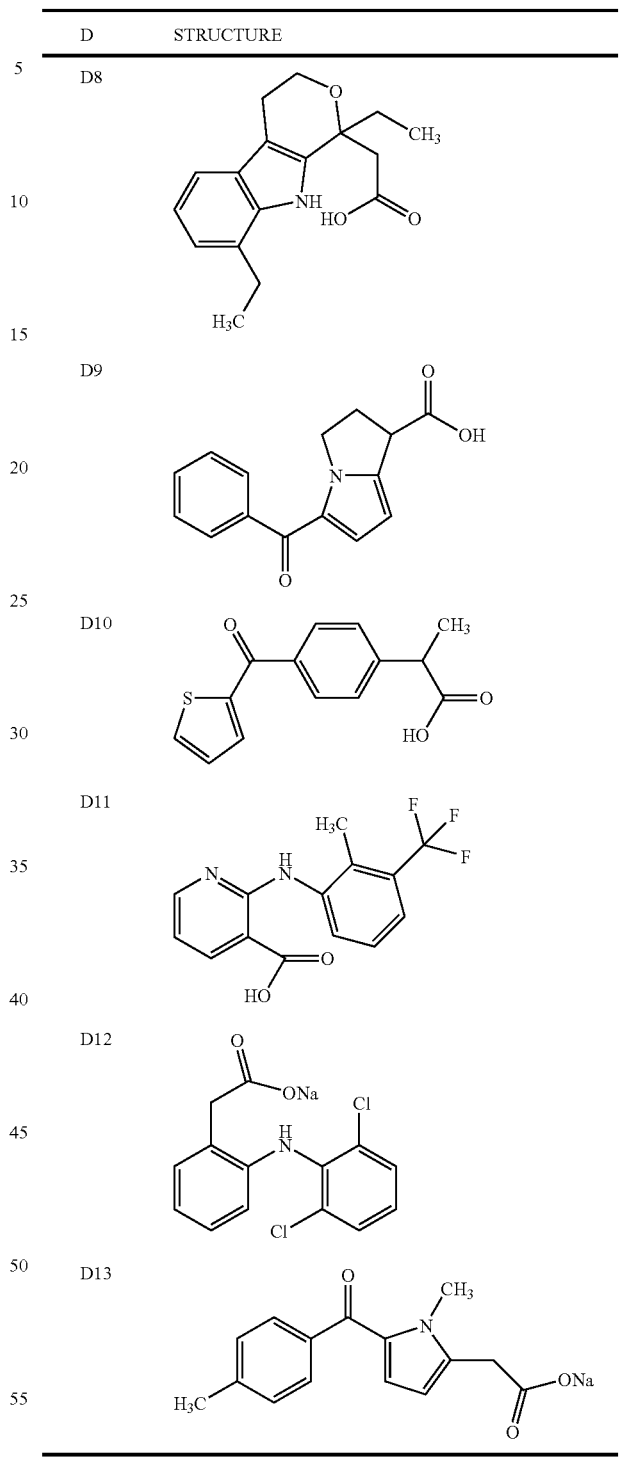

The compound D2 was S-(+)-ibuprofen; the remainder of the compounds with chiral centres were racemic mixtures. Compound D1 is indomethacin; D3 is flurbiprofen; D4 is naproxen, D5 is ketoprofen; D6 is acetyl salicylic acid; D7 is sulindac; D8 is etodolac; D9 is ketorolac; D10 is suprofen; D11 is flunixin, D12 is diclofenac sodium and D13 is tolmetin sodium.

Macrolide Subunits

TABLE 1

Formula IIA

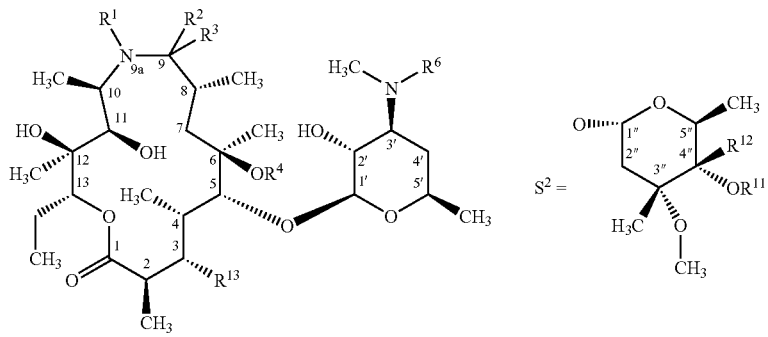

| Com. | M | $R^1$ | $R^2$ | $R^3$ | $R^4$ | $R^6$ | $R^{13}$ | $R^{11}$ | $R^{12}$ |
|---|---|---|---|---|---|---|---|---|---|
| $M_L1$ | M1 | L1 | H | H | H | $CH_3$ | $S^2$ | H | H |
| $M_L2$ | M1 | L2 | H | H | H | $CH_3$ | $S^2$ | H | H |
| $M_L3$ | M2 | L2 | H | H | H | $CH_3$ | OH | / | / |
| $M_L4$ | M3 | L2 | H | H | H | H | $S^2$ | H | H |
| $M_L5$ | M4 | L2 | H | H | H | $C_2H_5$ | $S^2$ | H | H |
| $M_L6$ | M5 | H | C=O | | $CH_3$ | $C_2H_5$ | $S^2$ | H | L3 |
| $M_L7$ | M6 | $CH_3$ | H | H | H | $CH_3$ | $S^2$ | L4 | H |

L1 = —$(CH_2)_3$—OH
L2 = —$(CH_2)_3$—$NH_2$
L3 = —$CH_2$—NH—$(CH_2)_2$—$NH_2$
L4 = —C(O)—$(CH_2)_2$—NH—$(CH_2)_2$—$NH_2$

The designation M1–M6 corresponds to macrolide subunits of the Formula IIA wherein the variables $R^1$–$R^{13}$ are as specified in the table.

EXAMPLE 1

Compound 1: (Formula I; M=M1, L=L1, D=D1)

To a solution of indomethacin (D1) (200 mg; 0.56 mmole) in dry DMF (3 ml) under argon was added 1,1-carbonyldiimidazole (187 mg; 1.15 mmol in 5 ml of DMF). The reaction mixture was stirred for 24 hours at −5° C., then was added compound $M_L1$ (443 mg; 0.56 mmole in 3 ml of DMF). The reaction mixture was heated 48 hours at 100° C., evaporated and purified on a silica gel column (eluant: $CHCl_3$:MeOH:$NH_4OH$=6:1:0.1). 56 mg of compound 1 was obtained; MS (m/z):1133[MH]$^+$. IR (KBr) cm$^{-1}$: 3449, 2972, 2936, 1731, 1686, 1622, 1564, 1546, 1512, 1478, 1460, 1374, 1323, 1263, 1225, 1168, 1089, 1057, 1013, 958, 925, 834, 804, 756, 732.

EXAMPLE 2

Compound 2: (Formula I; M=M1, L=L1, D=D2)

To a solution of S-(+)-ibuprofen (D2) (115 mg; 0.56 mmole) in dry DMF (3 ml) under argon was added 1,1-carbonyldiimidazole (187 mg; 1.15 mmol in 5 ml of DMF). The reaction mixture was stirred for 24 hours at −5° C., then was added compound $M_L1$ (443 mg; 0.56 mmole in 3 ml of DMF). The reaction mixture was heated 48 hours at 100° C., evaporated and purified on a silica gel column (eluant: $CHCl_3$:MeOH:$NH_4OH$=6:1:0.1). 43 mg of compound 2 was obtained; MS (m/z): 981.7[MH]$^+$. IR (KBr) cm$^{-1}$: 3483, 2971, 2937, 2873, 2787, 1733, 1655, 1638, 1561, 1511, 1459, 1421, 1379, 1332, 1248, 1167, 1109, 1055, 1013, 1000, 958, 900, 836, 803, 756, 728, 640.

EXAMPLE 3

Compound 3: (Formula I; M=M1, L=L1, D=D3)

To a solution of flurbiprofen (D3) (137 mg; 0.56 mmole) in dry DMF (3 ml) under argon was added 1,1-carbonyldiimidazole (187 mg; 1.15 mmol in 5 ml of DMF). The reaction mixture was stirred for 24 hours at −5° C., then was added compound $M_L1$ (443 mg; 0.56 mmole in 3 ml of DMF). The reaction mixture was heated 48 hours at 100° C., evaporated and purified on a silica gel column (eluant: $CHCl_3$:MeOH:$NH_4OH$=6:1:0.1). 46 mg of compound 3 was obtained; MS (m/z): 1119.5[MH]$^+$. IR (KBr) cm$^{-1}$: 3452, 2973, 2937, 2879, 2829, 2777, 1734, 1688, 1659, 1625, 1582, 1565, 1546, 1512, 1461, 1420, 1379, 1329, 1267, 1171, 1109, 1054, 1013, 999, 959, 899, 834, 801, 767, 726, 699, 640.

EXAMPLE 4

Compound 4: (Formula I; M=M1, L=L2, D=D1)

To a solution of indomethacin (D1) (104 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 127 mg of compound 4 was obtained. MS (m/z): 1131.8 [MH]$^+$. IR(KBr) cm$^{-1}$: 3451, 2971, 2936, 2829, 1722, 1675, 1659, 1542, 1595, 1563, 1546, 1529, 1478, 1461, 1374, 1323, 1260, 1227, 1168, 1110, 1089, 1054, 1013, 957, 927, 899, 834, 806, 755.

EXAMPLE 5

Compound 5: (Formula I; M=M1, L=L2, D=D2)

To a solution of (S)-(+)-ibuprofen (D2) (60 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon and then evaporated. Purification on a silica gel column (eluant: $CHCl_3$:MeOH:$NH_4OH$=6:1:0.1) gave 239 mg of compound 5. MS (m/z): 981.0 $[MH]^+$. IR (KBr) $cm^{-1}$: 3433, 2971, 2936, 2872, 1720, 1686, 1655, 1561, 1545, 1511, 1460, 1378, 1264, 1167, 1109, 1054, 1013, 1000, 958, 902, 835, 642.

EXAMPLE 6
Compound 6: (Formula I; M=M1, L=L2, D=D3)

To a solution of flurbiprofen (D3) (70 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon and then evaporated. Purification on a silica gel column eluting with $CHCl_3$:MeOH:$NH_4OH$=6:1:0.1 gave 160 mg of compound 6. MS (m/z): 1018.9 $[MH]^+$. IR (KBr) $cm^{-1}$: 3448, 2973, 2937, 2881, 2834, 2782, 1720, 1655, 1625, 1581, 1560, 1544, 1484, 1458, 1419, 1378, 1267, 1167, 1109, 1053, 1012, 958, 900, 835, 767, 726, 699, 641.

EXAMPLE 7
Compound 7: (Formula I; M=M1, L=L2, D=D4)

To a solution of naproxen (D4) (67 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon and concentrated under reduced pressure. Purification on a silica gel column eluting with $CHCl_3$:MeOH:$NH_4OH$=6:1:0.1 gave 162 mg of compound 7. MS (m/z): 1004.9 $[MH]^+$. IR (KBr) $cm^{-1}$: 3433, 2972, 2937, 2876, 2829, 2788, 1719, 1655, 1607, 1560, 1542, 1508, 1459, 1377, 1265, 1230, 1167, 1109, 1053, 1013, 1000, 958, 928, 895, 853, 809, 755, 640.

EXAMPLE 8
Compound 8: (Formula I; M=M1, L=L2, D=D5)

To a solution of ketoprofen (D5) (74 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon and concentrated under reduced pressure. Purification on a silica gel column eluting with $CHCl_3$:MeOH:$NH_4OH$=6:1:0.1 gave 114 mg of compound 8. MS (m/z): 1028.9 $[MH]^+$. IR (KBr) $cm^{-1}$: 3450, 3062, 2972, 2937, 2876, 2834, 2788, 1722, 1658, 1598, 1580, 1544, 1458, 1378, 1319, 1284, 1168, 1109, 1081, 1053, 1013, 1000, 957, 902, 834, 755, 723, 705, 643.

EXAMPLE 9
Compound 9: (Formula I; M=M1, L=L2, D=D6)

To a solution of acetylsalicylic acid (D6) (52 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon and concentrated under reduced pressure. Purification on a silica gel column eluting with $CHCl_3$:MeOH:$NH_4OH$=6:1:0.1 gave 127 mg of compound 9. MS (m/z): 955 $[MH]^+$.

EXAMPLE 10
Compound 10: (Formula I; M=M2, L=L2, D=D1)

Compound 4 (120 mg; 0.1 mmole) was dissolved in 3 mL 0.5 M HCl. The reaction mixture was stirred for 24 hours at room temperature. Then dichloromethane was added to the reaction mixture and layers were separated. The aqueous layer was adjusted to pH 10 and extracted with $CH_2Cl_2$. The combined organic extracts were washed with saturated $NaHCO_3$, dried over $MgSO_4$ and evaporated under reduced pressure. Purification on a silica gel column (eluant: EtOAc: TEA=96:4) gave 32 mg of compound 10. MS (m/z): 973.8 $[MH]^+$.

EXAMPLE 11
Compound 11: (Formula I; M=M2, L=L2, D=D2)

Compound 5 (120 mg; 0.1 mmole) was dissolved in 3 mL 0.5 M HCl. The reaction mixture was stirred for 24 hours at room temperature. Then dichloromethane was added to the reaction mixture and layers were separated. The aqueous layer was adjusted to pH 10 and extracted with $CH_2Cl_2$. The combined organic extracts were washed with saturated $NaHCO_3$, dried over $MgSO_4$ and evaporated under reduced pressure. Purification on a silica gel column (eluant: EtOAc: TEA=96:4) gave 28 mg of compound 11. MS (m/z): 822.1 $[MH]^+$. IR (KBr) $cm^{-1}$: 3450, 2971, 2873, 1710, 1656, 1544, 1511, 1459, 1380, 1350, 1262, 1173, 1111, 1073, 1050, 978, 957, 934, 898, 803, 755, 634.

EXAMPLE 12
Compound 12: (Formula I; M=M2, L=L2, D=D5)

Compound 8 (150 mg; 0.15 mmole) was dissolved in 5 mL 0.5 M HCl. The reaction mixture was stirred for 24 hours at room temperature. Then dichloromethane was added to the reaction mixture and layers were separated. The aqueous layer was adjusted to pH 10 and extracted with $CH_2Cl_2$. The combined organic extracts were washed with saturated $NaHCO_3$, dried over $MgSO_4$ and evaporated under reduced pressure. Purification on a silica gel column (eluant: EtOAc: TEA=96:4) gave 42 mg of compound 12. MS (m/z): 870.1 $[MH]^+$. IR (KBr) $cm^{-1}$: 3439, 3067, 2972, 2936, 2876, 1721, 1657, 1598, 1580, 1544, 1458, 1378, 1349, 1319, 1283, 1173, 1136, 1111, 1074, 1050, 1000, 956, 904, 863, 723, 705, 643.

EXAMPLE 13
Compound 13: (Formula I; M=M3, L=L2, D=D1)

The compound 4 (68 mg; 0.06 mmole) was dissolved in 10 mL of methanol. 38 mg (0.28 mmole) of $NaOAC \times 3H_2O$ and 15 mg (0.06 mmole) of $I_2$ were added. The reaction mixture was illuminated with a 500W halogen lamp for 2 h. Then, 2–3 drops of 0.1 M $Na_2S_2O_3$ were added. The solvent was then evaporated under reduced pressure and the residue was dissolved in ethyl-acetate and washed with water and saturated $NaHCO_3$ solution. The organic layer was dried over anhydrous $Na_2SO_4$ and evaporated. The product was purified on a silica gel column in the solvent system $CHCl_3$:MeOH:$NH_4OH$=6:1:0.1. The quantity of 32 mg of the compound 13 was isolated; MS (m/z): 1117.9 $[MH]^+$.

EXAMPLE 14

Compound 14: (Formula I; M=M4, L=L2, D=D1)

The compound 13 (100 mg; 0.09 mmole) was dissolved in 3 mL of methanol. To the solution, 127 µl of N,N-diisopropylethylamine and 45 µl of ethyliodide was added. The reaction mixture was stirred at a temperature of 50° C. for 20 hours. Subsequently, it was diluted with 30 mL of ethyl-acetate and washed with 30 mL of saturated aqueous sodium-hydrogencarbonate solution and 30 mL of water. The organic layer was dried over anhydrous sodium-sulphate. The solvent was evaporated by reduced pressure. The obtained mixture was purified on a silica gel column, eluent $CHCl_3$:MeOH:$NH_4OH$=6:1:0.1. The quantity of 48 mg of the compound 14 was obtained; MS (m/z): 1145.7 $[MH]^+$.

EXAMPLE 15

Compound 15: (Formula I; M=M5, L=L3, D=D1)

In 10 mL of dry dichlormethane, 84 mg of the indomethacin D1 (0.2 mmole) was dissolved in an inert atmosphere. Subsequently, 0.25 mL of triethylamine, 53 mg of hydroxybenzotriazole, 200 mg of the macrolide $M_L6$ (0.2 mmole) and 157 mg of 1-(3-dimethylaminopropyl)-3-ethyl-carbodiimide hydrochloride was added to the solution. The reaction mixture was stirred at room temperature overnight. The solvent was evaporated under reduced pressure and the obtained mixture was purified on a silica gel column, eluent $CHCl_3$:MeOH:$NH_4OH$=6:1:0.1. 130 mg of the compound 15 was obtained; MS (m/z): 1188.6 $[MH]^+$.

EXAMPLE 16

Compound 16: (Formula I; M=M6, L=L4, D=D1)

In 10 mL of dry dichlormethane, 43 mg of indomethacin D1 (0.1 mmole) was dissolved in an inert atmosphere. Subsequently, 0.12 mL of triethylamine, 32 mg of hydroxybenzotriazole, 103 mg of the macrolide $M_L7$ (0.1 mmole) and 82 mg of 1-(3-dimethylaminopropyl)-3-ethylcarbodiimide hydrochloride was added to the solution. The reaction mixture was stirred at room temperature overnight. The solvent was evaporated under reduced pressure and the obtained mixture was purified on a silica gel column, eluent $CHCl_3$:MeOH:$NH_4OH$=6:1:0.1. 80 mg of the compound 16 was obtained; MS (m/z): 1203.1 $[MH]^+$; MS (m/z): 981.0 $[MH]^+$. IR (KBr) $cm^{-1}$: 3424, 2972, 2936, 2833, 1734, 1678, 1595, 1562, 1544, 1526, 1477, 1459, 1374, 1324, 1258, 1225, 1179, 1108, 1090, 1073, 1039, 1015, 959, 926, 902, 836, 798, 755, 693, 666, 642.

EXAMPLE 17

Compound 17: (Formula I; M=M1, L=L2, D=D7)

To a solution of sulindac (D7) (103 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 262 mg of compound 17 was obtained. MS (m/z): 1130.3 $[MH]^+$.

EXAMPLE 18

Compound 18: (Formula I; M=M1, L=L2, D=D8)

To a solution of etodolac (D8) (83 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1).78 mg of compound 18 was obtained. MS (m/z): 1061.4 $[MH]^+$.

EXAMPLE 19

Compound 19: (Formula I; M=M1, L=L2, D=D9)

To a solution of ketorolac (D9) (74 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 110 mg of compound 19 was obtained. MS (m/z): 1029.5 $[MH]^+$. IR (KBr) $cm^{-1}$: 3448, 2972, 2936, 2876, 1719, 1655, 1624, 1572, 1561, 1544, 1492, 1465, 1430, 1400, 1379, 1342, 1272, 1167, 1109, 1052, 1013, 1000, 958, 894, 835, 797, 758, 724, 699, 670.

EXAMPLE 20

Compound 20: (Formula I; M=M1, L=L2, D=D10)

To a solution of suprofen (D10) (75 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 128 mg of compound 20 was obtained. MS (m/z): 1034.4 $[MH]^+$. IR (KBr) $cm^{-1}$: 3448, 3082, 2972, 2937, 2877, 2833, 2789, 1719, 1655, 1638, 1606, 1560, 1542, 1517, 1458, 1415, 1378, 1355, 1289, 1167, 1109, 1053, 1013, 1000, 958, 901, 886, 860, 845, 806, 753, 724, 665, 640.

EXAMPLE 21

Compound 21: (Formula I; M=M1, L=L2, D=D11)

To a solution of flunixin (D11) (86 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 76 mg of compound 21 was obtained. MS (m/z): 1070.4 $[MH]^+$. IR (KBr) $cm^{-1}$:

3451, 2973, 2938, 2881, 1722, 1642, 1593, 1524, 1462, 1379, 1321, 1321, 1278, 1259, 1168, 1121, 1081, 1053, 1020, 958, 899, 835, 795, 772, 721, 666, 640.

EXAMPLE 22

Compound 22: (Formula I; M=M1, L=L2, D=D12)

To a solution of diclofenac sodium (D12) (92 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 140 mg of compound 22 was obtained. MS (m/z): 1069.1 $[MH]^+$. IR (KBr) $cm^{-1}$: 3426, 3073, 2972, 2937, 2876, 2829, 2788, 1722, 1658, 1578, 1562, 1546, 1511, 1454, 1378, 1301, 1281, 1167, 1110, 1053, 1013, 999, 958, 898, 836, 750, 668.

EXAMPLE 23

Compound 23: (Formula I; M=M1, L=L2, D=D13)

To a solution of tolmetin sodium (D13) (80 mg; 0.29 mmole) in dry $CH_2Cl_2$ (5 ml) under argon, 0.380 mL (2.73 mmole) of triethylamine, 80 mg (0.59 mmole) of 1-hydroxybenzotriazole, 230 mg (0.29 mmole) of $M_L2$ and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume under reduced pressure and purified on a silica gel column (eluant: $CHCl_3$:MeOH:$NH_4OH$=6:1:0.1). 183 mg of compound 23 was obtained. MS (m/z): 1031.3 $[MH]^+$. IR (KBr) $cm^{-1}$: 3448, 2972, 2937, 2876, 1774, 1719, 1655, 1624, 1601, 1561, 1545, 1509, 1477, 1458, 1376, 1265, 1180, 1167, 1110, 1076, 1053, 1012, 1000, 957, 883, 834, 794, 751, 669, 639, 620.

---

What is claimed is:

1. A compound of Formula I:

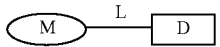
I wherein
M represents a group of
Formula II:

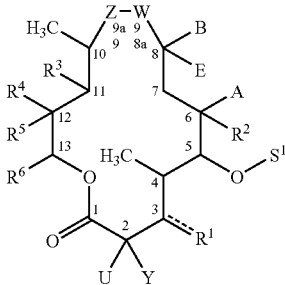
II wherein:
Z and W independently are: $>C=O$, $>CH_2$, $>CH-NR_tR_s$, $>N-R_N$ or $>C=N-R_M$ or a bond
wherein:
$R_t$ and $R_s$ independently are hydrogen or alkyl;
$R_M$ is hydroxy, alkoxy, substituted alkoxy or $OR^P$;
$R_N$ is hydrogen, $R^P$, alkyl, alkenyl, alkynyl, alkoxy, alkoxyalkyl, or $-C(X)-NR_tR_s$; wherein X is $=O$ or $=S$;
provided that Z and W cannot both simultaneously be, $>C=O$, $>CH_2$, $>CH-NR_tR_s$, $>N-R_N$ or $>C=N-R_M$ or a bond,
U and Y independently are hydrogen, halogen, alkyl, or hydroxyalkyl;
$R^1$ is hydroxy, $OR^P$, $-O-S^2$ group or an $=O$;
$S^1$ is a sugar moiety of formula:

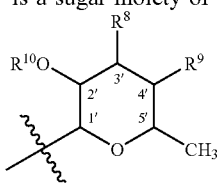

wherein
$R^8$ and $R^9$ are both hydrogen or together form a bond, or $R^9$ is hydrogen and $R^8$ is $-N(CH_3)R^y$, wherein $R^y$ is $R^P$, $R^z$ or $-C(O)R^z$ wherein $R^z$ is hydrogen or alkyl or alkenyl or alkynyl or cycloalkyl or aryl or heteroaryl or alkyl substituted with $C_2$-$C_7$-alkyl, $C_2$-$C_7$-alkenyl, $C_2$-$C_7$-alkynyl, aryl or heteroaryl
$R^{10}$ is hydrogen or $R^P$;
$S^2$ is a sugar moiety of formula:

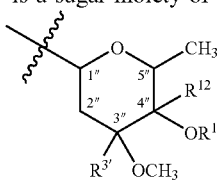

wherein:
$R^{3'}$ is hydrogen or methyl;
$R^{11}$ is hydrogen, $R^P$ or $O-R^{11}$ is a group that with $R^{12}$ and with C/4" carbon atom forms a $>C=O$ or epoxy group;
$R^{12}$ is hydrogen or a group that with $O-R^{11}$ group and with C/4" carbon atom forms a $>C=O$ or epoxy group;

$R^2$ is hydrogen, hydroxy, $OR^P$ or alkoxy
A is hydrogen or methyl;
B is methyl or epoxy;
E is hydrogen or halogen;
$R^3$ is hydroxy, $OR^P$, alkoxy or $R^3$ is a group that with $R^5$ and with C/11 and C/12 carbon atoms forms a cyclic carbonate or carbamate; or if W or Z is $>N-R_N$ $R^3$ is a group that with W or Z forms a cyclic carbamate;
$R^4$ is $C_1$-$C_4$ alkyl;
$R^5$ is hydrogen, hydroxy, $OR^P$, $C_1$-$C_4$-alkoxy, or a group that with $R^3$ and with C/11 and C/12 carbon atoms forms a cyclic carbonate or carbamate;
$R^6$ is hydrogen or $C_1$-$C_4$-alkyl; and
$R^P$ is hydroxyl or amino protective group;
wherein M has a linkage site through which it is linked to D via linking group L; provided that the linkage site is at one or more of the following:

a) any reactive hydroxy, nitrogen, or epoxy group located on $S^1$, $S^2$, or an aglycone oxygen if $S^1$ or/and $S^2$ is cleaved off;
b) a reactive $>N-R_N$ or $-NR_tR_s$ or $=O$ group located on Z or W;
c) a reactive hydroxy group located at any one of $R^1$, $R^2$, $R^3$, and $R^5$;
d) any other group that can be first derivatized to a hydroxy or $-NR_tR_s$ group; and D is derived from the NSAIDs selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.
L is a linker molecule to which each of M and D are covalently linked;
or a pharmaceutically acceptable salt or solvate thereof, or an individual diastereoisomer thereof.

2. A compound of Formula I:

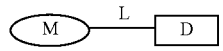
I wherein M represents a group of Formula II:

wherein:
Z and W independently are: >C=O, >CH$_2$, >CH—NR$_t$R$_s$, >N—R$_N$ or >C=N—R$_M$ or a bond
wherein:
R$_t$ and R$_s$ independently are hydrogen or alkyl;
R$_M$ is hydroxy, alkoxy, substituted alkoxy or OR$^p$;
R$_N$ is hydrogen, R$^p$, alkyl, alkenyl, alkynyl, alkoxy, alkoxyalkyl, or —C(X)—NR$_t$R$_s$; wherein X is =O or =S;
provided that Z and W cannot both simultaneously be, >C=O, >CH$_2$, >CH—NR$_t$R$_s$, >N—R$_N$ or >C=N—R$_M$ or a bond,
U and Y independently are hydrogen, halogen, alkyl, or hydroxyalkyl;
R$^1$ is hydroxy, OR$^p$, —O—S$^2$ group or an =O;
S$^1$ is a sugar moiety of formula:

wherein
R$^8$ and R$^9$ are both hydrogen or together form a bond, or R$^9$ is hydrogen and R$^8$ is —N(CH$_3$)R$^y$, wherein R$^y$ is R$^p$, R$^z$ or —C(O)R$^z$ wherein R$^z$ is hydrogen or alkyl or alkenyl or alkynyl or cycloalkyl or aryl or heteroaryl or alkyl substituted with C$_2$–C$_7$-alkyl, C$_2$–C$_7$-alkenyl, C$_2$–C$_7$-alkynyl, aryl or heteroaryl
R$^{10}$ is hydrogen or R$^p$;
S$^2$ is a sugar moiety of formula:

wherein:
R$^{3'}$ is hydrogen or methyl;
R$^{11}$ is hydrogen, R$^p$ or O—R$^{11}$ is a group that with R$^{12}$ and with C/4" carbon atom forms a >C=O or epoxy group;
R$^{12}$ is hydrogen or a group that with O—R$^{11}$ group and with C/4" carbon atom forms a >C=O or epoxy group;
R$^2$ is hydrogen, hydroxy, OR$^p$ or alkoxy
A is hydrogen or methyl;
B is methyl or epoxy;
E is hydrogen or halogen;

R$^3$ is hydroxy, OR$^p$, alkoxy or R$^3$ is a group that with R$^5$ and with C/11 and C/12 carbon atoms forms a cyclic carbonate or carbamate; or if W or Z is >N—R$_N$ R$^3$ is a group that with W or Z forms a cyclic carbamate;
R$^4$ is C$_1$–C$_4$ alkyl;
R$^5$ is hydrogen, hydroxy, OR$^p$, C$_1$–C$_4$-alkoxy, or a group that with R$^3$ and with C/11 and C/12 carbon atoms forms a cyclic carbonate or carbamate;
R$^6$ is hydrogen or C$_1$–C$_4$-alkyl; and
R$^p$ is hydroxyl or amino protective group;
wherein M has a linkage site through which it is linked to D via linking group L; provided that the linkage site is at one or more of the following:
a) any reactive hydroxy, nitrogen, or epoxy group located on S$^1$, S$^2$, or an aglycone oxygen if S$^1$ or/and S$^2$ is cleaved off;
b) a reactive >N—R$_N$ or —NR$_t$R$_s$ or =O group located on Z or W;
c) a reactive hydroxy group located at any one of R$^1$, R$^2$, R$^3$, and R$^5$;
d) any other group that can be first derivatized to a hydroxy or —NR$_t$R$_s$ group and
wherein L represents a group of Formula IV:

$$X^1-(CH_2)_m-Q-(CH_2)_n-X^2 \qquad IV$$

wherein
X$^1$ is selected from: —CH$_2$—, —C(O)—, OC(O)—, N—O— or —OC(O)NH—, —C(O)NH—;
X$^2$ is —NH— or —NHC(O)—, —OC(O)—, —C(O)—, —O— or —CH$_2$—;
Q is —NH— or —CH$_2$—, or absent;
wherein each —CH$_2$— or —NH— group may be optionally substituted by C$_1$–C$_7$-alkyl, C$_2$–C$_7$-alkenyl, C$_2$–C$_7$-alkynyl, C(O)R$^x$, C(O)OR$^x$, C(O)NHR$^x$ wherein R$^x$ is C$_1$–C$_7$-alkyl, aryl or heteroaryl;
the symbols m and n independently are a whole number from 0 to 4, with the proviso that if Q is NH, n cannot be 0.
wherein D is derived from the NSAIDs selecting from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.

or a pharmaceutically acceptable salt or solvate thereof.

3. A compound according to claim 2 wherein Z and W together are: —N(CH$_3$)—CH$_2$—, —NH—CH$_2$—, —CH$_2$—NH—, —C(O)—NH— or —NH—C(O)—;

A and B are methyl;

E is hydrogen;

R$^2$ is hydroxy or methoxy;

S$^1$ represents desosamine sugar wherein R$^8$ is selected from: hydrogen, methyl, amino, C$_1$–C$_6$ alkylamino or C$_1$–C$_6$ dialkylamino;

R$^9$ and R$^{10}$ are hydrogen;

R$^1$ is hydroxy or the O—S$^2$ group wherein the S$^2$ represents a cladinose sugar wherein:
R$^{11}$ is hydrogen, or O—R$^{11}$ is a group that with R$^{12}$ and with C/4" carbon atom forms a >C=O or epoxy group; R$^{12}$ is hydrogen or a group that with O—R$^{11}$ and with C/4" carbon atom forms a >C=O or epoxy group;
R$^{13}$ is methyl;

U is hydrogen

Y is methyl;

R$^6$ is hydroxy, methyl or ethyl;

R$^5$ is hydrogen, hydroxy, methoxy or a group that with R$^3$ and with C/11 and C/12 carbon atoms forms a cyclic carbonate or carbamate bridge;

R$^3$ is hydroxy or a group that forms a cyclic carbamate bridge with W or Z, or R$^3$ is a group that with R$^5$ and with C/11 and C/12 carbon atoms forms a cyclic carbonate or carbamate bridge;

R$^4$ is methyl;

provided that the linkage is through the nitrogen of Z at N/9a position or through the carbon of R$^{12}$ or through the oxygen of R$^{11}$ both at C/4" position of the S$^2$ sugar.

4. A compound according to claim 2 wherein

X$^1$ is —CH$_2$— or —OC(O)—;

X$^2$ is —NHC(O)—;

Q is —NH— or absent.

5. A compound according to claim 2 wherein

D is derived from a NSAID selecting from the group consisting of: S-(+)-ibuprofen, indomethacin, flurbiprofen, naproxen, ketoprofen, acetyl salicylic acid, sulindac, etodolac, ketorolac, suprofen, flunixin, diclofenac sodium and tolmetin sodium.

6. A compound of the formula or a pharmaceutically acceptable salt or solvate thereof.

7. A compound of the formula or a pharmaceutically acceptable salt or solvate thereof.

8. A compound of the formula
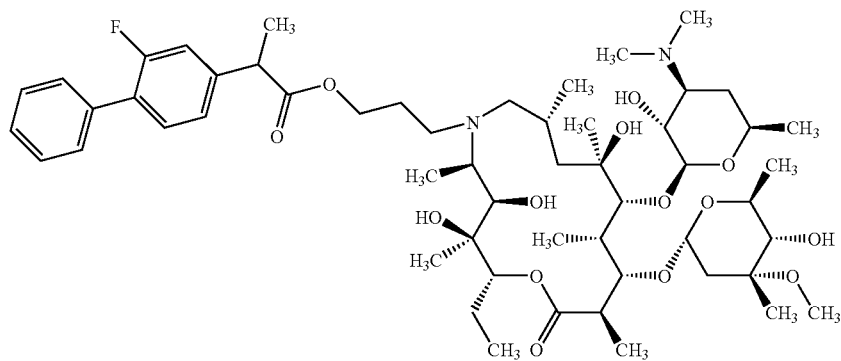
or a pharmaceutically acceptable salt or solvate thereof.
9. A compound of the formula
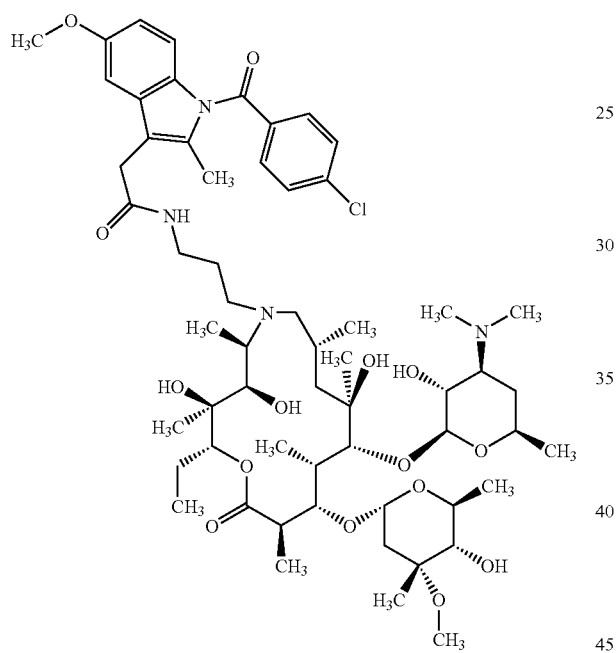
or a pharmaceutically acceptable salt or solvate thereof.
10. A compound of the formula
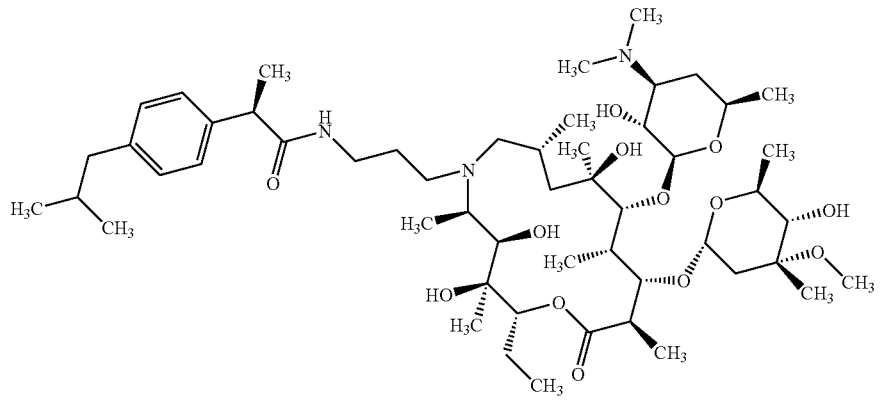
or a pharmaceutically acceptable salt or solvate thereof.

11. A compound of the formula

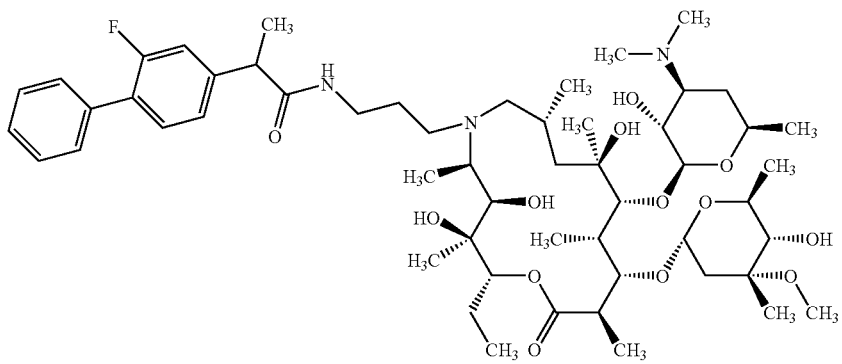

or a pharmaceutically acceptable salt or solvate thereof.

12. A compound of the formula

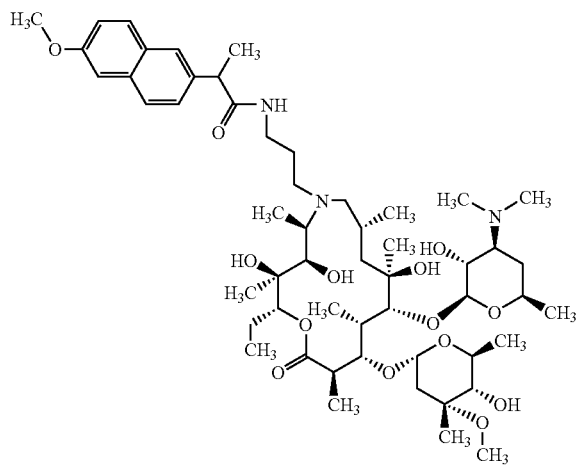

or a pharmaceutically acceptable salt or solvate thereof.

13. A compound of the formula

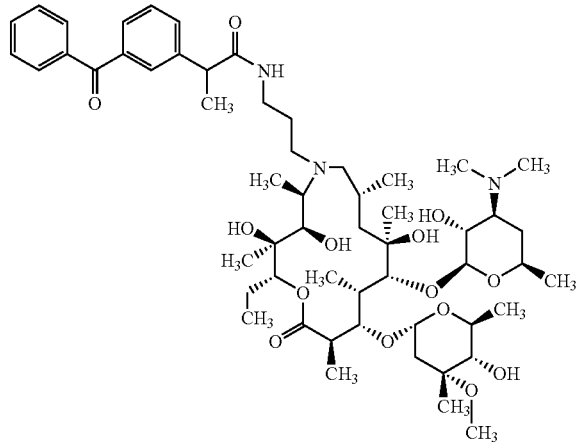

or a pharmaceutically acceptable salt or solvate thereof.

14. A compound of the formula

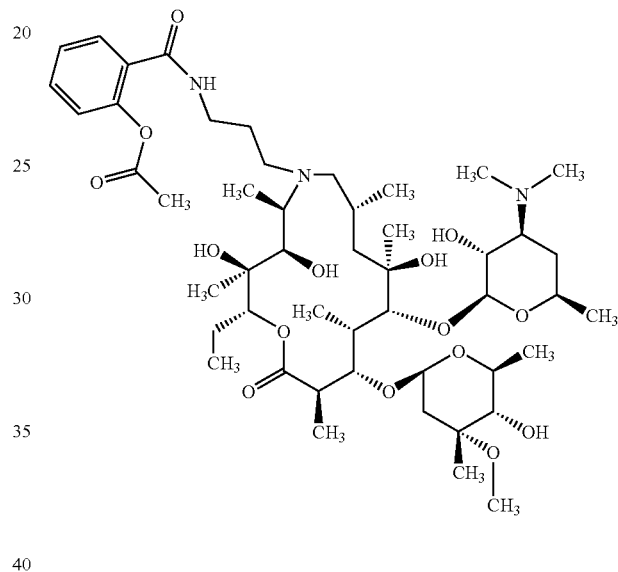

or a pharmaceutically acceptable salt or solvate thereof.

15. A compound of the formula

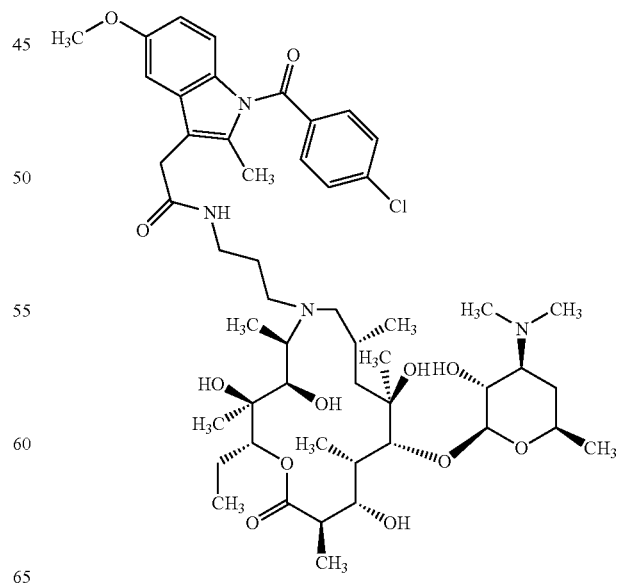

or a pharmaceutically acceptable salt or solvate thereof.

16. A compound of the formula
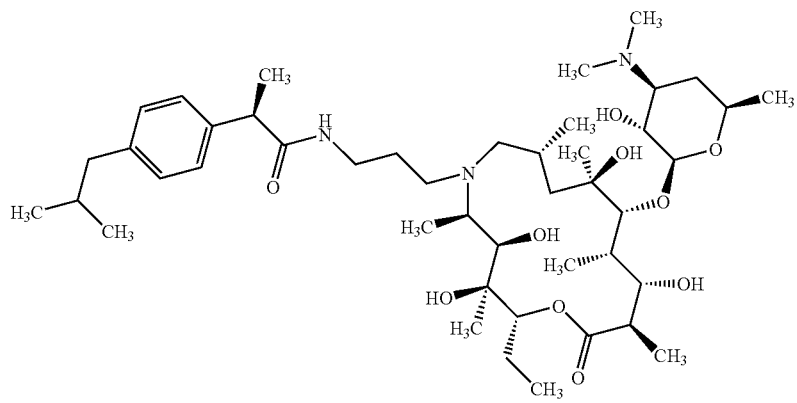
or a pharmaceutically acceptable salt or solvate thereof.
17. A compound of the formula
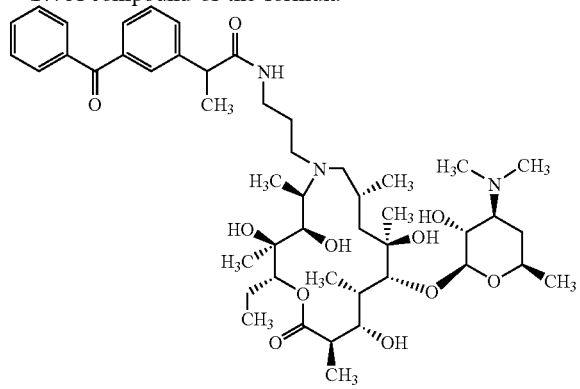
or a pharmaceutically acceptable salt or solvate thereof.
18. A compound of the formula
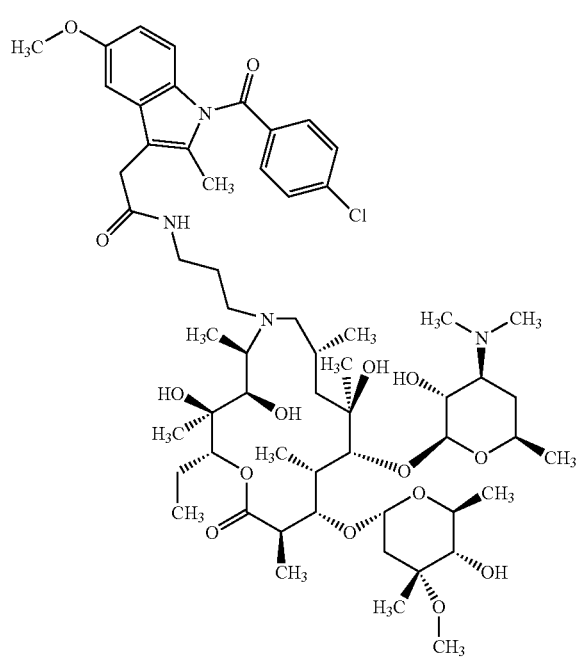
or a pharmaceutically acceptable salt or solvate thereof.
19. A compound of the formula
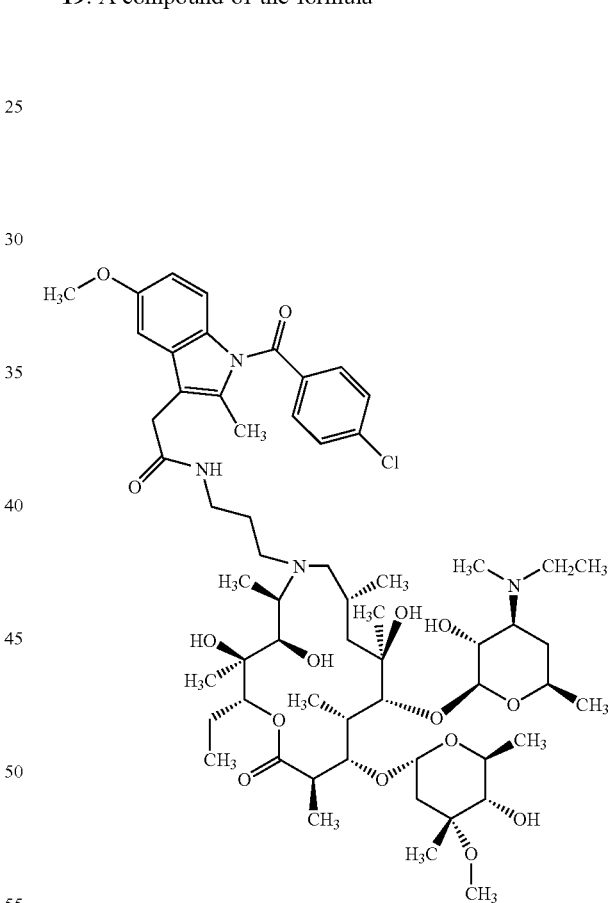
or a pharmaceutically acceptable salt or solvate thereof.

20. A compound of the formula
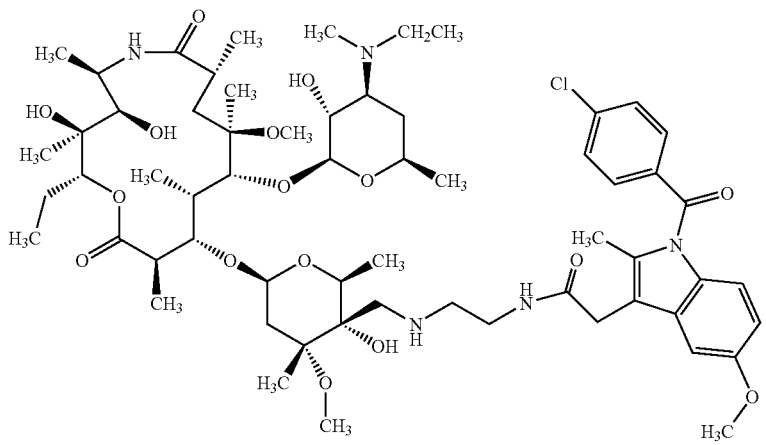
or a pharmaceutically acceptable salt or solvate thereof.
21. A compound of the formula
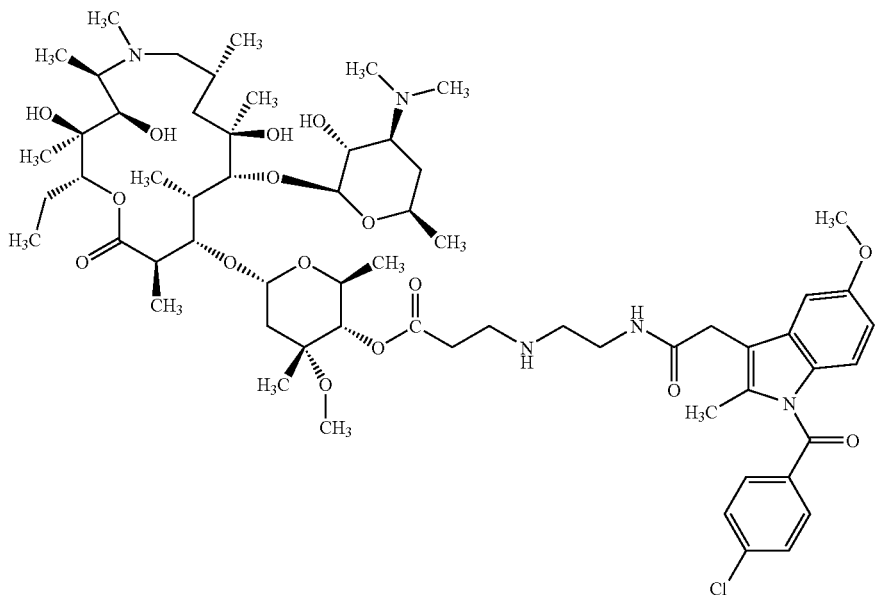
or a pharmaceutically acceptable salt or solvate thereof.

22. A compound of the formula
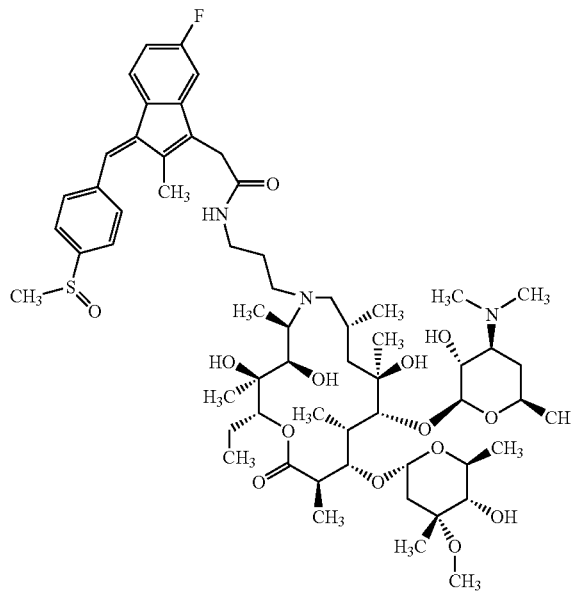
or a pharmaceutically acceptable salt or solvate thereof.
23. A compound of the formula
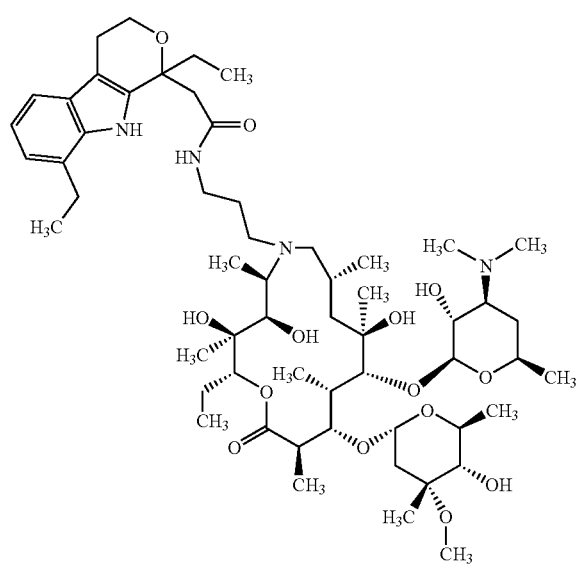
or a pharmaceutically acceptable salt or solvate thereof.
24. A compound of the formula
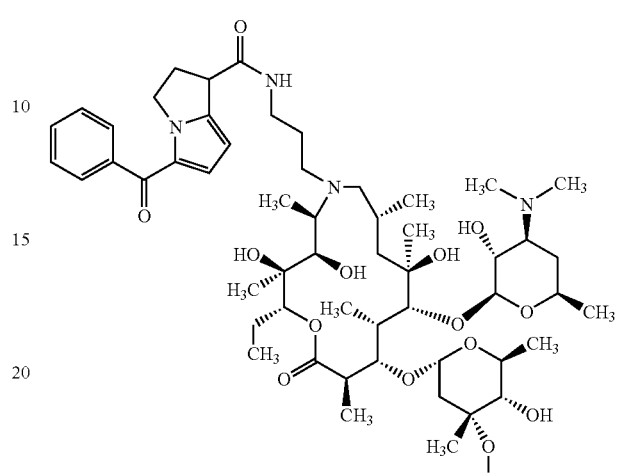
or a pharmaceutically acceptable salt or solvate thereof.
25. A compound of the formula
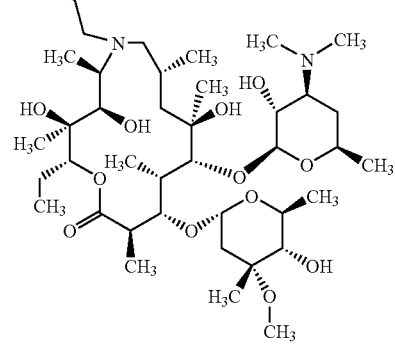
or a pharmaceutically acceptable salt or solvate thereof.

26. A compound of the formula

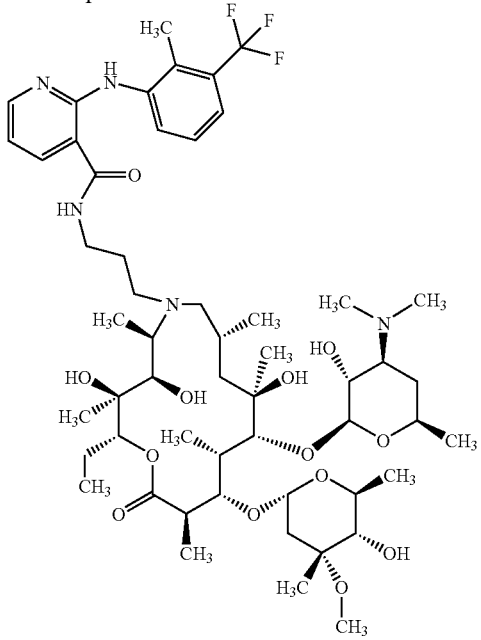

or a pharmaceutically acceptable salt or solvate thereof.

27. A compound of the formula

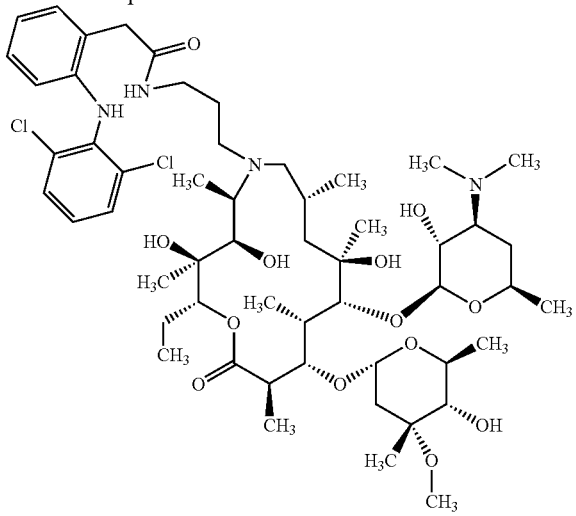

or a pharmaceutically acceptable salt or solvate thereof.

28. A compound of the formula

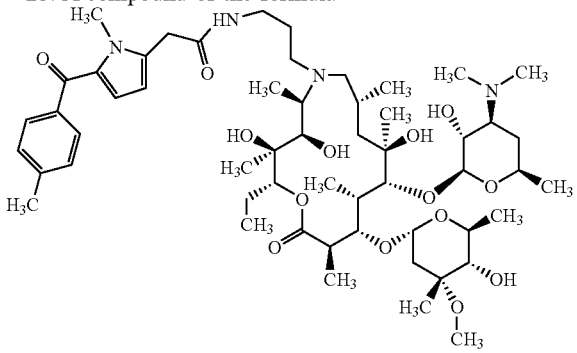

or a phamaceutically acceptable salt or solvate thereof.

29. A process for the preparation a compound of Formula I

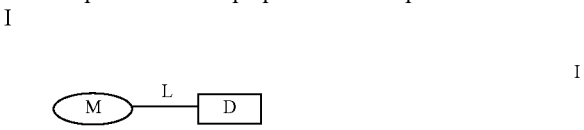

wherein

M represents a group of

Formula II:

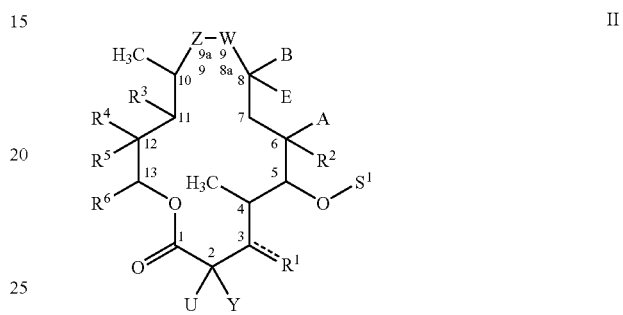

wherein:

Z and W independently are: >C=O, >CH$_2$, >CH—NR$_t$R$_s$, >N—R$_N$ or >C=N—R$_M$ or a bond wherein:

R$_t$ and R$_s$ independently are hydrogen or alkyl;

R$_M$ is hydroxy, alkoxy, substituted alkoxy or OR$^P$;

R$_N$ is hydrogen, R$^P$, alkyl, alkenyl, alkynyl, alkoxy, alkoxyalkyl, or —C(X)—NR$_t$R$_s$; wherein X is =O or =S;

provided that Z and W cannot both simultaneously be, >C=O, >CH$_2$, >CH—NR$_t$R$_s$, >N—R$_N$ or >C=N—R$_M$ or a bond, U and Y independently are hydrogen, halogen, alkyl, or hydroxyalkyl;

R$^1$ is hydroxy, OR$^P$, —O—S$^2$ group or an =O;

S$^1$ is a sugar moiety of formula:

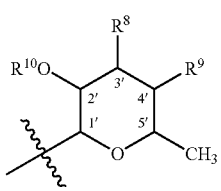

wherein

R$^8$ and R$^9$ are both hydrogen or together form a bond, or R$^9$ is hydrogen and R$^8$ is —N(CH$_3$)R$^y$, wherein R$^y$ is R$^P$, R$^z$ or —C(O)R$^z$ wherein R$^z$ is hydrogen or alkyl or alkenyl or alkynyl or cycloalkyl or aryl or heteroaryl or alkyl substituted with C$_2$–C$_7$-alkyl, C$_2$–C$_7$-alkenyl, C$_2$–C$_7$-alkynyl, aryl or heteroaryl R$^{10}$ is hydrogen or R$^P$;

$S^2$ is a sugar moiety of formula:

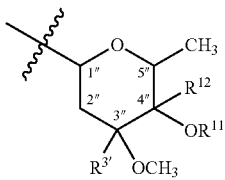

wherein:
$R^{3'}$ is hydrogen or methyl;
$R^{11}$ is hydrogen, $R^p$ or $O-R^{11}$ is a group that with $R^{12}$ and with C/4" carbon atom forms a $>C=O$ or epoxy group;
$R^{12}$ is hydrogen or a group that with $O-R^{11}$ group and with C/4" carbon atom forms a $>C=O$ or epoxy group;
$R^2$ is hydrogen, hydroxy, $OR^p$ or alkoxy
A is hydrogen or methyl;
B is methyl or epoxy;
E is hydrogen or halogen;
$R^3$ is hydroxy, $OR^p$, alkoxy or $R^3$ is a group that with $R^5$ and with C/11 and C/12 carbon atoms forms a cyclic carbonate or carbamate; or if W or Z is $>N-R_N$ $R^3$ is a group that with W or Z forms a cyclic carbamate;
$R^4$ is $C_1-C_4$ alkyl;
$R^5$ is hydrogen, hydroxy, $OR^p$, $C_1-C_4$-alkoxy, or a group that with $R^3$ and with C/11 and C/12 carbon atoms forms a cyclic carbonate or carbamate;
$R^6$ is hydrogen or $C_1-C_4$-alkyl; and
$R^p$ is hydroxyl or amino protective group;
wherein M has a linkage site through which it is linked to D via linking group L; provided that the linkage site is at one or more of the following:
  a) any reactive hydroxy, nitrogen, or epoxy group located on $S^1$, $S^2$, or an aglycone oxygen if $S^1$ or/and $S^2$ is cleaved off;
  b) a reactive $>N-R_N$ or $-NR_rR_s$ or $=O$ group located on Z or W;
  c) a reactive hydroxy group located at any one of $R^1$, $R^2$, $R^3$, and $R^5$;
  d) any other group that can be first derivatized to a hydroxy or $-NR_rR_s$ group; and
wherein L represents a group of
Formula IV:

$$X^1-(CH_2)_m\text{-}Q\text{-}(CH_2)_n-X^2 \qquad IV$$

wherein
$X^1$ is selected from: $-CH_2-$, $-C(O)-$, $OC(O)-$, $N-O-$ or $-OC(O)NH-$, $-C(O)NH-$;
$X^2$ is $-NH-$ or $-NHC(O)-$, $-OC(O)-$, $-C(O)-$, $-O-$ or $-CH_2-$;
Q is $-NH-$ or $-CH_2-$, or absent;
  wherein each $-CH_2-$ or $-NH-$ group may be optionally substituted by $C_1-C_7$-alkyl, $C_2-C_7$-alkenyl, $C_2-C_7$-alkynyl, $C(O)R^x$, $C(O)OR^x$, $C(O)NHR^x$ wherein $R^x$ is $C_1-C_7$-alkyl, aryl or heteroaryl;
the symbols m and n independently are a whole number from 0 to 4, with the proviso that if Q is NH, n cannot be 0.
wherein D is derived from the NSAIDs selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.
which comprises:
a) for a compound of Formula I, where $X^2$ is $-NHC(O)-$, by reacting a compound of Formula V:

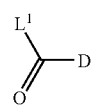

wherein $L^1$ represents a leaving group, and a free amino group of a macrolide represented by Formula VIa:

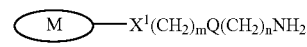

b) for a compound of Formula I, where $X^2$ is $-OC(O)-$, by reacting a compound of Formula V and the free hydroxyl group of a macrolide represented by Formula VIb:

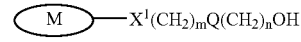

c) for a compound of Formula I, wherein $X^1$ is $-OC(O)-$, Q is $-NH-$ and $X^2$ is $-NHC(O)-$, by reacting a macrolide represented by formula:

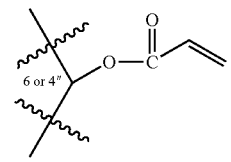

and a free amino group of the compound represented by formula:

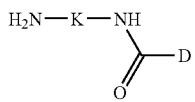

d) for a compound of Formula I, where $X^1$ is —OC(O)NH— and $X^2$ is —NHC(O)—, by reacting a macrolide represented by formula

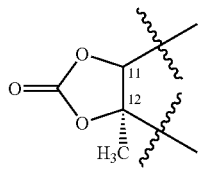

and free amino group of the compound represented by formula:

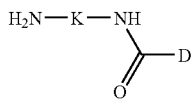

e) for a compound of Formula I, where $X^1$ is —CH$_2$—, Q is —NH— and $X^2$ is —NHC(O)—, by reacting a macrolide represented by formula:

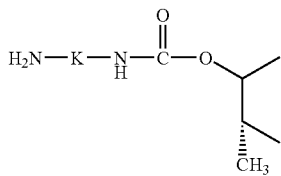

and a compound of Formula V;

f) for a compound of Formula I by reacting a macrolide represented by Formula VIIf or by Formula VIIg or by Formula VIIh having a leaving group $L^2$

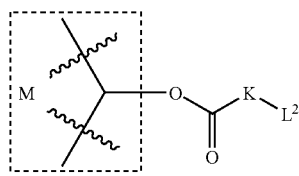
VIIf

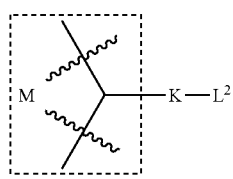
VIIg

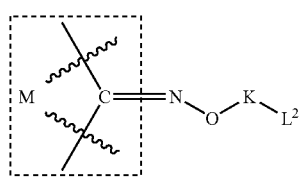
VIIh with a free carboxylic acid of nonsteroidal anti-inflammatory subunit.

30. A pharmaceutical composition comprising a compound according to claim 1 as well as a pharmaceutically acceptable diluent or carrier.

31. A method of treating inflammatory diseases, disorders or conditions characterized by or associated with an undesirable inflammatory immune response, and all diseases and conditions induced by or associated with an excessive secretion of TNF-α and IL-1 which comprises administering to a subject in need of treatment a therapeutically effective amount of a compound according to claim 1.

32. A method of treating inflammatory conditions or immune or anaphylactic disorders associated with infiltration of leukocytes into inflamed tissue in a subject in need thereof which comprises administering to said subject a therapeutically effective amount of a compound according to claim 1.

33. The method according to claim 32, wherein inflammatory conditions and immune disorders are selected from the group consisting of asthma, adult respiratory distress syndrome, bronchitis, and cystic fibrosis.

34. A method according to claim 32, wherein said inflammatory conditions and immune disorders are selected from the group consisting of inflammatory conditions or immune disorders of the lungs, joints, eyes, bowel, skin, and heart.

35. A method according to claim 32, wherein said inflammatory conditions and immune disorders are selected from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

36. A method for abating inflammation in an affected organ or tissue comprising delivering to said organ or tissue a therapeutically effective amount of a compound according to claim 1.

37. A pharmaceutical composition comprising a compound according to claim 2 as well as a pharmaceutically acceptable diluent or carrier.

38. A method of treating inflammatory diseases, disorders or conditions characterized by or associated with an undesirable inflammatory immune response, and all diseases and conditions induced by or associated with an excessive secretion of TNF-α and IL-1 which comprises administering to a subject in need of treatment a therapeutically effective amount of a compound according to claim 2.

39. A method of treating inflammatory conditions or immune or anaphylactic disorders associated with infiltration of leukocytes into inflamed tissue in a subject in need thereof which comprises administering to said subject a therapeutically effective amount of a compound according to claim 2.

40. The method according to claim 39, wherein inflammatory conditions and immune disorders are selected from the group consisting of asthma, adult respiratory distress syndrome, bronchitis, and cystic fibrosis.

41. A method according to claim 39, wherein said inflammatory conditions and immune disorders are selected from the group consisting of inflammatory conditions or immune disorders of the lungs, joints, eyes, bowel, skin, and heart.

42. A method according to claim 39, wherein said inflammatory conditions and immune disorders are selected from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

43. A method for abating inflammation in an affected organ or tissue comprising delivering to said organ or tissue a therapeutically effective amount of a compound according to claim 2.

44. A compound of Formula I:

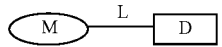

I wherein

M represents a group of

Formula II:

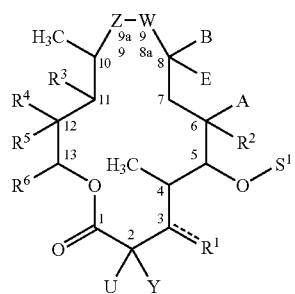

II wherein:

Z and W independently are: $>C=O$, $>CH_2$, $>CH-NR_tR_s$, $>N-R_N$ or $>C=N-R_M$ or a bond wherein:

$R_t$ and $R_s$ independently are hydrogen or alkyl;

$R_M$ is hydroxy, alkoxy, substituted alkoxy or $OR^P$;

$R_N$ is hydrogen, $R^P$, alkyl, alkenyl, alkynyl, alkoxy, alkoxyalkyl, or $-C(X)-NR_tR_s$; wherein X is $=O$ or $=S$;

provided that Z and W cannot both simultaneously be, $>C=O$, $>CH_2$, $>CH-NR_tR_s$, $>N-R_N$ or $>C=N-R_M$ or a bond, U and Y independently are hydrogen, halogen, alkyl, or hydroxyalkyl;

$R^1$ is hydroxy, $OR^P$, $-O-S^2$ group or an $=O$;

$S^1$ is a sugar moiety of formula:

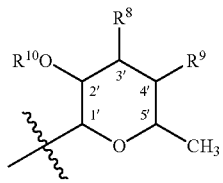

wherein $R^8$ and $R^9$ are both hydrogen or together form a bond, or $R^9$ is hydrogen and $R^8$ is $-N(CH_3)R^y$, wherein $R^y$ is $R^p$, $R^z$ or $-C(O)R^z$ wherein $R^z$ is hydrogen or alkyl or alkenyl or alkynyl or cycloalkyl or aryl or heteroaryl or alkyl substituted with $C_2-C_7$-alkyl, $C_2-C_7$-alkenyl, $C_2-C_7$-alkynyl, aryl or heteroaryl $R^{10}$ is hydrogen or $R^p$;

$S^2$ is a sugar moiety of formula:

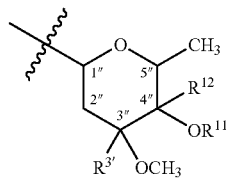

wherein:

$R^{3'}$ is hydrogen or methyl;

$R^{11}$ is hydrogen, $R^p$ or $O-R^{11}$ is a group that with $R^{12}$ and with C/4" carbon atom forms a $>C=O$ or epoxy group;

$R^{12}$ is hydrogen or a group that with $O-R^{11}$ group and with C/4" carbon atom forms a $>C=O$ or epoxy group;

$R^2$ is hydrogen, hydroxy, $OR^p$ or alkoxy

A is hydrogen or methyl;

B is methyl or epoxy;

E is hydrogen or halogen;

$R^3$ is hydroxy, $OR^p$, alkoxy or $R^3$ is a group that with $R^5$ and with C/11 and C/12 carbon atoms forms a cyclic carbonate or carbamate; or if W or Z is $>N-R_N$ $R^3$ is a group that with W or Z forms a cyclic carbamate;

$R^4$ is $C_1-C_4$ alkyl;

$R^5$ is hydrogen, hydroxy, $OR^p$, $C_1-C_4$-alkoxy, or a group that with $R^3$ and with C/11 and C/12 carbon atoms forms a cyclic carbonate or carbamate;

$R^6$ is hydrogen or $C_1-C_4$-alkyl; and $R^p$ is hydroxyl or amino protective group;

wherein M has a linkage site through which it is linked to D via linking group L; provided that the linkage site is at one or more of the following:

a) any reactive hydroxy, nitrogen, or epoxy group located on $S^2$, or an aglycone oxygen when $S^1$ or/and $S^2$ is cleaved off; wherein if both $S^1$ and $S^2$ is cleaved off, D cannot be acetyl salicylic acid;

b) a reactive $>N-R_N$ or $-NR_tR_s$ or $=O$ group located on Z or W; wherein if Z is $-N(R_N)$ and W is $-CH_2$, and M is linked to D $R_N$, D can not be meclofenamic acid or ibuprofen; and c) a reactive hydroxy group located at any one of $R^1$, $R^2$, $R^3$, and $R^5$;

D is derived from the NSAIDs selected from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acethylsalicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.

L is a linker molecule to which each of M and D are covalently linked;

or a pharmaceutically acceptable salt or solvate thereof, or an individual diastereoisomer thereof.

45. A compound of Formula I:

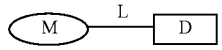

wherein M represents a group of Formula II:

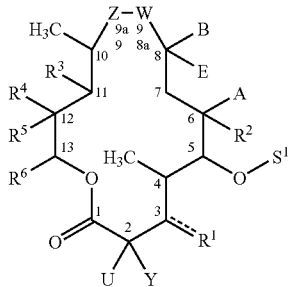

wherein:

Z and W independently are: $>C=O$, $>CH_2$, $>CH-NR_tR_s$, $>N-R_N$ or $>C=N-R_M$ or a bond wherein:

$R_t$ and $R_s$ independently are hydrogen or alkyl;

$R_M$ is hydroxy, alkoxy, or $OR^P$;

$R_N$ is hydrogen, $R^P$, alkyl, alkenyl, alkynyl, alkoxy, alkoxyalkyl, or $-C(X)-NR_tR_s$; wherein X is $=O$ or $=S$;

provided that Z and W cannot both simultaneously be, $>C=O$, $>CH_2$, $>CH-NR_tR_s$, $>N-R_N$ or $>C=N-R_M$ or a bond, U and Y independently are hydrogen, halogen, alkyl, or hydroxyalkyl;

$R^1$ is hydroxy, $OR^P$, $-O-S^2$ group or an $=O$;

$S^1$ is a sugar moiety of formula:

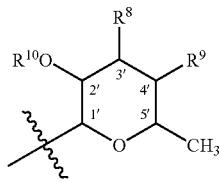

wherein $R^8$ and $R^9$ are both hydrogen or together form a bond, or $R^9$ is hydrogen and $R^8$ is $-N(CH_3)R^y$, wherein $R^y$ is $R^P$, $R^z$ or $-C(O)R^z$ wherein $R^z$ is hydrogen or alkyl or alkenyl or alkynyl or cycloalkyl or aryl or heteroaryl or alkyl substituted with $C_2-C_7$-alkyl, $C_2-C_7$-alkenyl, $C_2-C_7$-alkynyl, aryl or heteroaryl $R^{10}$ is hydrogen or $R^P$;

$S^2$ is a sugar moiety of formula:

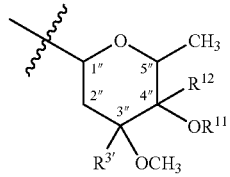

wherein:

$R^{3'}$ is hydrogen or methyl;

$R^{11}$ is hydrogen, $R^P$;

$R^{12}$ is hydrogen;

$R^2$ is hydrogen, hydroxy, $OR^P$ or alkoxy

A is hydrogen or methyl;

B is methyl or epoxy;

E is hydrogen or halogen;

$R^3$ is hydroxy, $OR^P$, alkoxy or $R^3$ is a group that with $R^5$ and with C/11 and C/12 carbon atoms forms a cyclic carbonate or carbamate; or if W or Z is $>N-R_N$ $R^3$ is a group that with W or Z forms a cyclic carbamate;

$R^4$ is $C_1-C_4$ alkyl;

$R^5$ is hydrogen, hydroxy, $OR^P$, $C_1-C_4$-alkoxy, or a group that with $R^3$ and with C/11 and C/12 carbon atoms forms a cyclic carbonate or carbamate;

$R^6$ is hydrogen or $C_1-C_4$-alkyl; and $R^P$ is hydroxyl or amino protective group;

wherein M has a linkage site through which it is linked to D via linking group L; provided that the linkage site is at one or more of the following:

a) any reactive hydroxy, nitrogen, or epoxy group located on $S^2$, the C4' position of $S^1$, or an aglycone oxygen when $S^1$ or/and $S^2$ is cleaved off; wherein if both $S^1$ and $S^2$ are cleaved off, D cannot be acetyl salicylic acid;

b) a reactive $>N-R_N$ or $-NR_tR_s$ or $=O$ group located on Z or W; wherein if Z is $-N(R_N)$ and W is $-CH_2$, and M is linked to D via $R_N$, D can not be meclofenamic acid or ibuprofen;

c) a reactive hydroxy group located at any one of $R^2$, $R^3$, and $R^5$;

D is derived from the NSAIDs selecting from the group consisting of: aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celexocib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O- acetyl acid, salicylsulphuric acid, salicin, salicylamide, salsalate, sulindac, suprofen, suxibutazone, tamoxifen, tenoxicam, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporin.

L is a linker molecule to which each of M and D are covalently linked;

or a pharmaceutically acceptable salt or solvate thereof.

* * * * *